United States Patent
Kato et al.

(10) Patent No.: US 10,382,678 B2
(45) Date of Patent: Aug. 13, 2019

(54) IMAGE GENERATION APPARATUS AND IMAGE GENERATION METHOD

(71) Applicant: Panasonic Intellectual Property Management Co., Ltd., Osaka (JP)

(72) Inventors: Yumiko Kato, Osaka (JP); Yoshihide Sawada, Tokyo (JP); Yasuhiro Mukaigawa, Nara (JP); Takuya Funatomi, Nara (JP); Hiroyuki Kubo, Nara (JP); Fusataka Kuniyoshi, Okinawa (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 31 days.

(21) Appl. No.: 15/898,888

(22) Filed: Feb. 19, 2018

(65) Prior Publication Data
US 2018/0255240 A1    Sep. 6, 2018

(30) Foreign Application Priority Data

Mar. 1, 2017 (JP) .................................. 2017-038826

(51) Int. Cl.
*H04N 5/232* (2006.01)
*G01N 21/64* (2006.01)
(Continued)

(52) U.S. Cl.
CPC ..... *H04N 5/23232* (2013.01); *G01N 21/4788* (2013.01); *G01N 21/6458* (2013.01);
(Continued)

(58) Field of Classification Search
CPC ........... G01N 21/4788; G01N 21/6458; G02B 21/0004; G02B 21/06; G02B 21/365;
(Continued)

(56) References Cited

U.S. PATENT DOCUMENTS 6,905,838 B1    6/2005 Bittner
9,438,793 B2 *  9/2016 Adachi .............. H04N 5/23232
(Continued)

FOREIGN PATENT DOCUMENTS

JP    2003-529747    10/2003
JP    2010-019762    1/2010
(Continued)

OTHER PUBLICATIONS

Shree K. Nayar et al., "Fast Separation of Direct and Global Components of a Scene using High Frequency Illumination", ACM Transactions on Graphics-Proceedings of ACM SIGGRAPH 2006, vol. 25 Issue 3, Jul. 2006.

*Primary Examiner* — Mekonen T Bekele
(74) *Attorney, Agent, or Firm* — Wenderoth, Lind & Ponack, L.L.P.

(57) ABSTRACT

An image generation apparatus includes first and second light sources, an image sensor, a mask, and a processing circuit. The image sensor acquires a first image when the first light source is energized and acquires a second image when the second light source is energized. The processing circuit obtains a pixel value based on a direct light component or a pixel value based on a component other than the direct light component corresponding to a focal point by using pixel values of first pixel regions of the first image, pixel values of second pixel regions of the second image, the ratios of the direct light and the light other than the direct light from the first light source, and the ratios of the direct light and the light other than the direct light from the second light source and generates a cross-sectional image of a substance on the focal plane.

4 Claims, 20 Drawing Sheets

(51) Int. Cl.
*G01N 21/47* (2006.01)
*H04N 5/349* (2011.01)
*G02B 21/00* (2006.01)
*G06K 9/20* (2006.01)
*G06K 9/00* (2006.01)
*H04N 5/225* (2006.01)
*H04N 5/235* (2006.01)
*G01B 11/00* (2006.01)
*G01B 11/25* (2006.01)

(52) U.S. Cl.
CPC ..... *G02B 21/0004* (2013.01); *G06K 9/00134* (2013.01); *G06K 9/2036* (2013.01); *H04N 5/349* (2013.01); *G01B 11/002* (2013.01); *G01B 11/2527* (2013.01); *H04N 5/2256* (2013.01); *H04N 5/2354* (2013.01)

(58) Field of Classification Search
CPC ............. G02B 21/367; G06K 9/00134; G06K 9/2036; G06K 9/0014; G06K 9/00147; G06K 9/2027; G06K 9/6223; H04N 5/23232; H04N 5/349; H04N 5/2256; H04N 5/2354; G01B 11/002; G01B 11/2527; G06T 7/0012; G06T 7/73; G06T 2207/10056; G06T 2207/30024; G06T 2207/30044; G06T 2207/30242
See application file for complete search history.

(56) References Cited

U.S. PATENT DOCUMENTS

| | | | |
|---|---|---|---|
| 2009/0273829 A1 | 11/2009 | Terakawa et al. | |
| 2011/0181801 A1* | 7/2011 | Okumura | G03B 21/28 349/5 |
| 2014/0133702 A1* | 5/2014 | Zheng | G06K 9/00624 382/103 |
| 2014/0233008 A1* | 8/2014 | Tanitsu | G03F 7/70116 355/71 |
| 2015/0172575 A1* | 6/2015 | Adachi | H04N 5/2354 348/239 |
| 2018/0210185 A1* | 7/2018 | Kato | G06K 9/2027 |

FOREIGN PATENT DOCUMENTS

| | | |
|---|---|---|
| WO | 2007/063909 | 6/2007 |
| WO | 2014/196203 | 12/2014 |

* cited by examiner

FIG. 9

| IMAGE ID | ILLUMINATION POSITION |
|---|---|
| ⋮ | ⋮ |
| 001145 | (2301, 1741) |
| 001146 | (2321, 1741) |
| ⋮ | ⋮ |

FIG. 10

| PIXEL ON IMAGE SENSOR | ILLUMINATION POSITION | COEFFICIENT α OF DIRECT LIGHT COMPONENT | COEFFICIENT β OF SCATTERED LIGHT COMPONENT |
|---|---|---|---|
| ⋮ | ⋮ | ⋮ | ⋮ |
| (2101, 1501) | (2301, 1741) | 0.78 | 0.46 |
|  | (2321, 1741) | 0.69 | 0.48 |
| ⋮ | ⋮ | ⋮ | ⋮ |
| (2160, 1587) | (2341, 1681) | 0.32 | 0.45 |
| ⋮ | ⋮ | ⋮ | ⋮ |

IMAGE GENERATION APPARATUS AND IMAGE GENERATION METHOD

BACKGROUND

1. Technical Field

The present disclosure relates to an image generation apparatus, such as a lensless microscope, for generating an image and an image generation method.

2. Description of the Related Art

Demand for continuously observing cultured cells without staining the cells has been on the rise in many fields in which cultured cells are used for medical and industrial purposes, such as production of cells for use in medical treatment and investigation of the efficacy of a medicine. However, since most cells are almost colorless and transparent, the contrast of the image of the cells captured through an optical microscope using transmitted light is low. As a result, it is difficult to observe the cells. One of the reasons for the low contrast is scattering or refraction of light by the medium around the object or the object itself.

Japanese Patent No. 5403458 describes a method for removing noise components of reflected light by using the brightness in the bright state that occurs when a light beam is emitted and the brightness in the dark state that occurs when emission of the light beam is stopped.

In addition, Japanese Patent No. 5789766 describes a method for providing a dark-field microscope with a wide field of view by capturing the image under illumination with a bright-and-dark pattern so that a transparent object is observed.

Note that continuous observation of cultured cells is carried out in a limited space called an incubator for maintaining a humid environment for culturing cells. For observation in such a limited space, Japanese Patent No. 5789766 and U.S. Patent Application Publication No. 2014/0133702 disclose a lensless microscope capable of observing minute cells without using a lens. By using such a technique, a high-resolution image is generated from a plurality of images captured under illumination from a plurality of different positions.

In addition, a method for expressing the result of capturing an image under illumination with a bright-and-dark pattern by using an expression using the direct light component and the light component other than the direct light component is described in June 2006 ACM Transactions on Graphics (TOG)—Proceedings of ACM SIGGRAPH 2006, Volume 25 Issue 3, July 2006 (hereinafter, referred to as "Non-Patent Literature (NPL) 1").

SUMMARY

However, the method described in Japanese Patent No. 5403458 has a disadvantage in that the apparatus increases in size. That is, in this method, parallel light and a digital micromirror device are used in an apparatus for measuring the irregularities of the surface of an object by recording the brightness of the reflected illumination light. Thereafter, the difference between the brightness recorded by emitting light of a first bright-and-dark pattern and the brightness recorded by emitting a second bright-and-dark pattern is obtained. By using the difference, relative brightness is obtained. In this manner, the brightness values at the positions of an objective lens are easily compared with one another. However, to spread the bright-and-dark pattern over the entire area of an image sensor, a lens is needed and, thus, the apparatus increases in size. In addition, according to the method described in Japanese Patent No. 5789766, the refracting light at the boundary surface of the object is extracted from the result of capturing the image under illumination with a bright-and-dark pattern. The focal point is determined by the lens and, thus, the apparatus increases in size, as in Japanese Patent No. 5789766.

Furthermore, when capturing the image under illumination from multiple light sources as in Japanese Patent No. 5789766 and U.S. Patent Application Publication No. 2014/0133702, it is necessary to change the position of the illumination. To capture an image while changing the position of the light source and the position of the digital micromirror device, the apparatus increases in size. Consequently, it is difficult to combine the technique of reversal of brightness and darkness by the digital micromirror device with the lensless microscope.

In NPL 1, an expression using the direct light component and the light component other than the direct light component is proposed. However, the bright-and-dark pattern needs to be moved. When the structure to move the bright-and-dark pattern is mounted in the lensless microscope, the system increases in size.

One non-limiting and exemplary embodiment provides an image generation apparatus capable of generating an image that allows any cross section of a substance to be easily observed while preventing an increase in the size of the image generation apparatus.

In one general aspect, the techniques disclosed here feature an image generation apparatus including a first light source, a second light source located a predetermined distance away from the first light source, an image sensor on which a translucent substance is disposed, a mask located between the image sensor and the first and second light sources and having a light-transmitting portion that transmits light emitted from the first light source and light emitted from the second light source and a light-shielding portion that blocks light emitted from the first light source and light emitted from the second light source, and a processing circuit. The image sensor acquires a first image of the substance when the first light source is energized and acquires a second image of the substance when the second light source is energized. The first image has a plurality of first pixel regions, and the second image has a plurality of second pixel regions. The processing circuit (a) acquires information regarding a focal plane located between the image sensor and the mask and having a plurality of focal points, (b) acquires, for each of the first pixel regions, a ratio of first light including direct light that is emitted from the first light source, travels straight without being refracted and/or scattered, and is incident on the image sensor, and a ratio of second light including light other than the direct light that is emitted from the first light source and is incident on the image sensor, acquires, for each of the second pixel regions, a ratio of third light including direct light that is emitted from the second light source, travels straight without being refracted and/or scattered, and is incident on the image sensor, and a ratio of fourth light including light other than the direct light that is emitted from the second light source and is incident on the image sensor, (c) acquires, by using pixel values of the plurality of the first pixel regions of the first image, pixel values of the plurality of the second pixel regions of the second image, the ratio of the first light, the ratio of the second light, the ratio of the third light, and the ratio of the fourth light, a pixel value based on the first light and the third light for each of the plurality of focal points or a pixel value based on the second light and the fourth light for each of the plurality of focal points, and (d) generates a cross-sectional image of the substance on the focal plane by using the pixel value based on the first light and the third light for each of the plurality of focal points or the pixel value based on the second light and the fourth light for each of the plurality of focal points.

It should be noted that general or specific embodiments may be implemented as a system, a method, an integrated circuit, a computer program, a computer-readable storage medium, or any selective combination thereof. Examples of a computer-readable storage medium include a nonvolatile recording medium, such as a compact disc-read only memory (CD-ROM).

According to the present disclosure, an image that enables any cross section of a substance to be easily observed can be provided without increasing the size of the apparatus. Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 9 illustrates an example of information stored in a storage unit according to the first embodiment;

FIG. 10 illustrates an example of a coefficient map held in a coefficient map holding unit according to the first embodiment;

DETAILED DESCRIPTION

Figure 1:
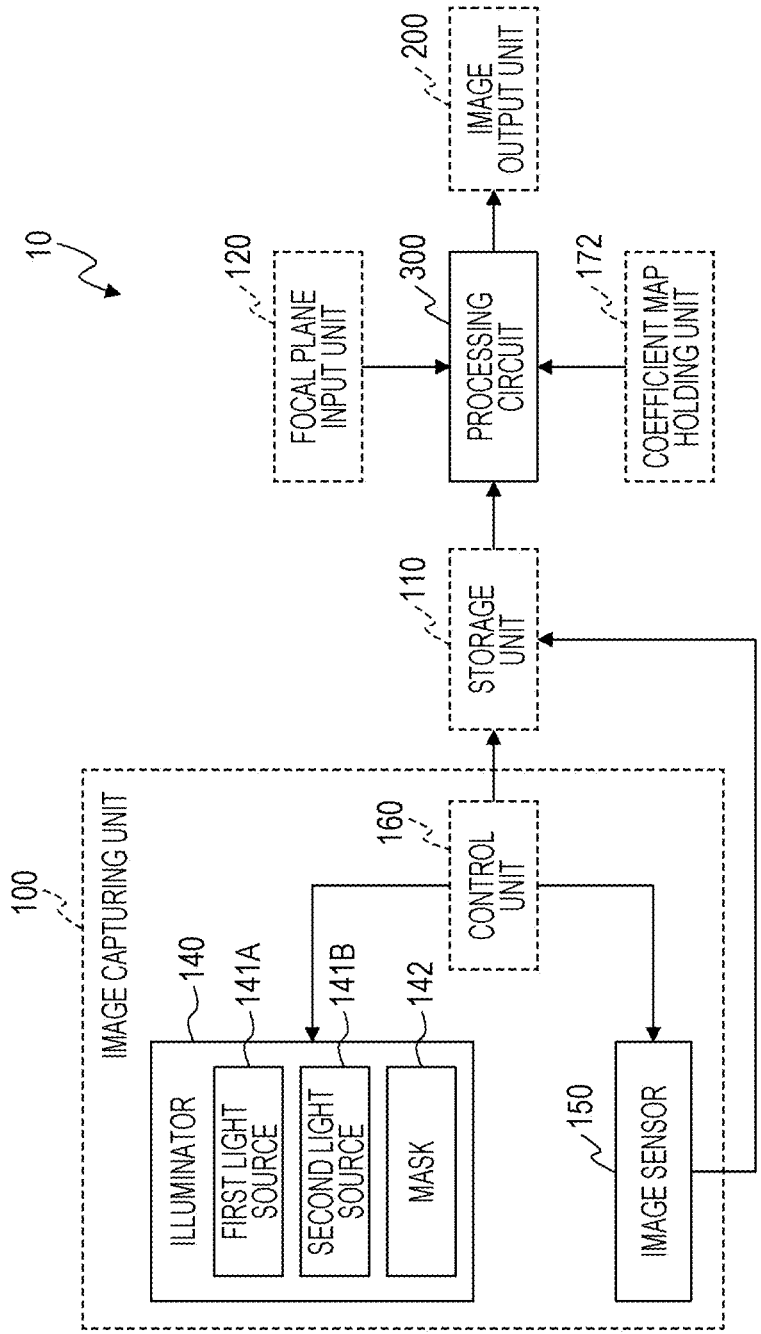
FIG. 1 is a functional block diagram of an image generation apparatus according to a first embodiment.

Before describing the details of embodiments of the present disclosure, a description of the terms and various aspects of the disclosure is described.

Definition of Terms

Direct light is "light incident from the light source onto the image sensor without being refracted and/or scattered". Note that the direct light is light that travels straight through a medium, further travels straight through the boundary surface between the medium and an object and the inside of the object, and is incident on the image sensor. When the light travelling straight hits the boundary surface of the translucent substance, part of the light travels straight and the other part of the light is refracted at the boundary surface. In addition, part of the light travelling straight hits a scattering material in the object and scatters. The light other than the direct light may include light other than the light travelling straight through the boundary surface between the medium and the object and the inside of the object, that is, scattered light and/or refracted light. Note that the above-mentioned object is an object (for example, a cell) whose image is to be captured by the image sensor. However, the object may be any translucent substance other than a cell.

Variety of Aspects of Disclosure

According to an aspect of the present disclosure, an image generation apparatus includes a first light source, a second light source located a predetermined distance away from the first light source, an image sensor on which a translucent substance is disposed, a mask located between the image sensor and the first and second light sources and having a light-transmitting portion that transmits light emitted from the first light source and light emitted from the second light source and a light-shielding portion that blocks light emitted from the first light source and light emitted from the second light source, and a processing circuit. The image sensor acquires a first image of the substance when the first light source is energized and acquires a second image of the substance when the second light source is energized. The first image has a plurality of first pixel regions, and the second image has a plurality of second pixel regions. The processing circuit (a) acquires information regarding a focal plane located between the image sensor and the mask and having a plurality of focal points, (b) acquires, for each of the first pixel regions, a ratio of first light including direct light that is emitted from the first light source, travels straight without being refracted and/or scattered, and is incident on the image sensor, and a ratio of second light including light other than the direct light that is emitted from the first light source and is incident on the image sensor, acquires, for each of the second pixel regions, a ratio of third light including direct light that is emitted from the second light source, travels straight without being refracted and/or scattered, and is incident on the image sensor, and a ratio of fourth light including light other than the direct light that is emitted from the second light source and is incident on the image sensor, (c) acquires, by using pixel values of the plurality of the first pixel regions of the first image, pixel values of the plurality of the second pixel regions of the second image, the ratio of the first light, the ratio of the second light, the ratio of the third light, and the ratio of the fourth light, a pixel value based on the first light and the third light for each of the plurality of focal points or a pixel value based on the second light and the fourth light for each of the plurality of focal points, and (d) generates a cross-sectional image of the substance on the focal plane by using the pixel value based on the first light and the third light for each of the plurality of focal points or the pixel value based on the second light and the fourth light for each of the plurality of focal points. More specifically, in operation (c), let α1, β1, α2, β2, L1, and L2 be the ratio of the first light, the ratio of the second light, the ratio of the third light, the ratio of the fourth light, the pixel value of the first pixel region, and the pixel value of the second pixel region corresponding to one of the plurality of focal points, respectively. Then, a pixel value D based on the first light and the third light corresponding to the focal point and a pixel value G based on the second light and the fourth light corresponding to the focal point may be obtained by solving the following equation by using a least squares method:

$$\begin{bmatrix} L1 \\ L2 \end{bmatrix} = \begin{bmatrix} \alpha1 & \beta1 \\ \alpha2 & \beta2 \end{bmatrix} \begin{bmatrix} D \\ G \end{bmatrix}.$$

Thus, a cross-sectional image of the substance on a focal plane is generated by using the pixel value based on the first light and the third light corresponding to each of the plurality of focal points, that is, the pixel value (more particularly, the brightness value) based on the direct light component. Alternatively, a cross-sectional image of the substance on the focal plane is generated by using the pixel value based on the second light and the fourth light corresponding to each of the plurality of focal points, that is, the pixel value (more particularly, the brightness value) based on the light component other than the direct light component. The cross-sectional image of the substance generated by using the pixel values based on the direct light component can clearly indicate the outline of the substance, while the cross sectional image of the substance generated by using the pixel values of the light component other than direct light component can clearly indicate a region including a light scattering substance inside the substance. As a result, the image of a desired cross section of the substance that is easily observed can be generated by controlling the focal plane.

In addition, the pixel value based on the direct light component corresponding to each of a plurality of focal points or the pixel value based on the light component other than the direct light component corresponding to each of a plurality of focal points is obtained by using the pixel values of the plurality of first pixel regions of the first image, the pixel values of the plurality of second pixel regions of the second image, the ratio of the first light, the ratio of the second light, the ratio of the third light, and the ratio of the fourth light. That is, separation of the direct light component from the light component other than the direct light component and calculation for refocusing are performed at the same time. As a result, the processing speed can be improved, and the processing load can be reduced.

Furthermore, by switching among the light sources that illuminate the substance, the first image and the second image having different bright-and-dark patterns can be acquired. That is, it is unnecessary to change the position of a structure, such as a light source or a digital micromirror device, in order to acquire the first image and the second image having different bright-and-dark patterns and, thus, the apparatus can be reduced in size.

As a result, an image that enables a desired cross section of the substance to be easily observed can be generated without increasing the size of the image generation apparatus.

It should be noted that general or specific embodiments may be implemented as an apparatus, a method, an integrated circuit, a computer program, a computer-readable storage medium, such as a CD-ROM, or any selective combination thereof.

An image generation apparatus and an image generation method according to an embodiment of the present disclosure are described in detail below with reference to the accompanying drawings.

Each of the embodiments described below is a particular example of the present disclosure. A value, a shape, a constituent element, the positions and the connection form of the constituent elements, steps, and the sequence of steps described in the embodiments are only examples and shall not be construed as limiting the scope of the present disclosure. In addition, among the constituent elements in the embodiments described below, the constituent element that does not appear in an independent claim, which has the broadest scope, is described as an optional constituent element, First Embodiment The image generation apparatus according to the first embodiment includes a plurality of point light sources, an illuminator including a mask in which a light-transmitting portion that transmits light and a light-shielding portion that blocks light are formed, such as a slit pattern or a checker pattern, an image sensor, and a processing circuit. A plurality of point light sources disposed in the illuminator at different positions sequentially illuminate an object (that is, a substance) located on the image sensor. At this time, the image sensor captures the image of the object while switching between the bright-and-dark patterns of the light reaching the image sensor and the object. As a result, a plurality of images captured with different bright-and-dark patterns are obtained. The processing circuit determines a focal plane on which an in-focus image is to be generated and determines a point on the image sensor corresponding to a pixel on the focal plane (hereinafter, the point is referred to as a corresponding point).

Subsequently, the processing circuit expresses the observed brightness of the obtained point by the sum of the direct light component and the light component other than the direct light component. Thereafter, the processing circuit obtains the direct light component and the light component other than the direct light component common to all of the corresponding points by optimization using the least squares method. The direct light component and the light component other than the direct light component common to all of the corresponding points are those at the position of a pixel of the focal plane (that is, the focal position). By generating an image by using the obtained direct light components and light components other than the direct light components, it is possible to generate an in-focus image from the direct light components and an in-focus image from the light components other than the direct light components. The in-focus image generated from the direct light components indicates the boundary surface of the object, while the in-focus image generated from the light components other than the direct light components indicates the distribution of the scattering substance contained in the object. Note that the direct light component is also referred to as a "Direct component", and the light component other than the direct light component is also referred to as a "Global component". In addition, according to the present embodiment, the light other than the direct light includes not only light generated by scattering of direct light emitted from the point light source but also light generated by refraction of the direct light.

Note that according to the present embodiment, an object whose image is to be captured is, for example, a cell. However, the object may be any substance that is translucent other than a cell.

1 Configuration of Image Generation Apparatus

FIG. 1 is a functional block diagram of an image generation apparatus 10 according to a first embodiment. The image generation apparatus 10 generates the image of a substance that is translucent, such as a cell. As illustrated in FIG. 1, the image generation apparatus 10 includes an image capturing unit 100, a storage unit 110, a processing circuit 300, a focal plane input unit 120, a coefficient map holding unit 172, and an image output unit 200. The image capturing unit 100 includes an illuminator 140, an image sensor 150, and a control unit 160. Although the image generation apparatus 10 according to the first embodiment includes the control unit 160, the storage unit 110, the focal plane input unit 120, the coefficient map holding unit 172, and the image output unit 200, these constituent elements are not always needed, and the image generation apparatus 10 does not necessarily have to include these constituent elements.

Figure 2:
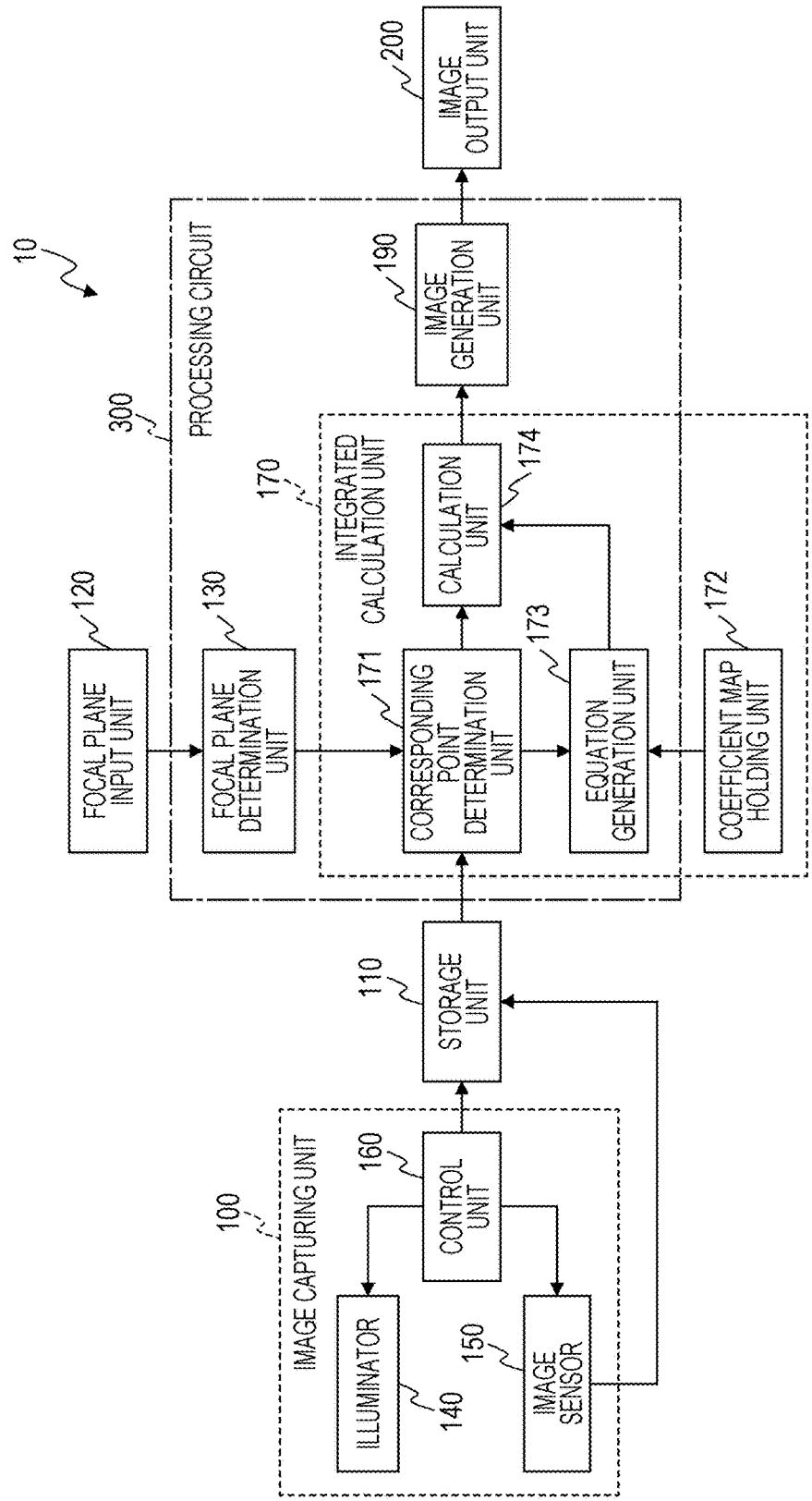
FIG. 2 is a functional block diagram of the image generation apparatus illustrating the detailed functional configuration of a processing circuit according to the first embodiment.

FIG. 2 is a functional block diagram of the image generation apparatus 10 illustrating the functional configuration of the processing circuit 300 according to the first embodiment in detail.

The processing circuit 300 includes a focal plane determination unit 130, a corresponding point determination unit 171, an equation generation unit 173, a calculation unit 174, and an image generation unit 190. An integrated calculation unit 170 includes the corresponding point determination unit 171, the equation generation unit 173, the calculation unit 174, and the coefficient map holding unit 172.

1-1 Image Capturing Unit

The configuration of the image capturing unit 100 is described first. As described above, the image capturing unit 100 includes the illuminator 140, the image sensor 150, and the control unit 160. The image capturing unit 100 captures the image (a photographic image) of a substance, which is an object. In this example, the image capturing unit 100 does not have a focus lens.

The illuminator 140 according to the first embodiment includes a first light source 141A, a second light source 141B, and a mask 142. The first light source 141A is a point light source that illuminates the substance. The second light source 141B is a point light source that illuminates the substance from a position a predetermined distance away from the first light source 141A. The mask 142 has a light-transmitting portion that enables light rays from the first light source 141A and the second light source 141B to pass therethrough and a light-shielding portion that blocks the light rays from passing therethrough. The mask 142 is located between the image sensor 150 and each of the first light source 141A and the second light source 141B. Note that the predetermined distance is a distance that is equal to ⅓ or ⅔ of a cycle (described below).

The illuminator 140 is described in detail below.

Figure 3:
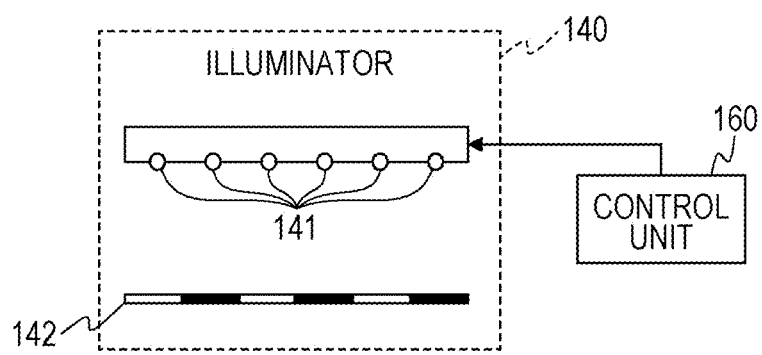
FIG. 3 is a schematic illustration of an example of the structure of an illuminator according to the first embodiment.

FIG. 3 is a schematic illustration of an example of the configuration of the illuminator 140 according to the first embodiment. More specifically, the illuminator 140 includes a plurality of point light sources 141 including the above-described first light source 141A and second light source 141B. The illuminator 140 further includes the mask 142. The mask 142 has a slit or checker pattern. That is, the mask 142 has a light-transmitting portion that transmits light and a light-shielding portion that blocks light.

Figure 4:
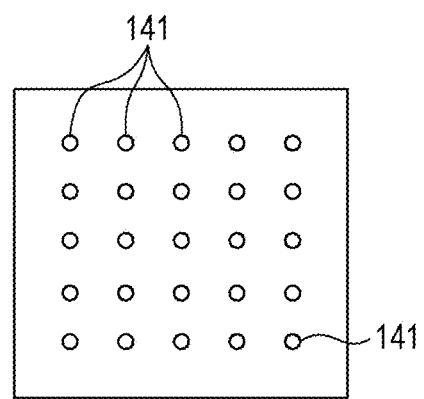
FIG. 4 is a schematic illustration of an example of the arrangement of a plurality of point light sources according to the first embodiment.

FIG. 4 is a schematic illustration of an example of the arrangement of the plurality of point light sources 141. In the example illustrated in FIG. 4, the plurality of point light sources 141 are arranged at equal intervals. Each of the point light sources 141 has, for example, a light emitting surface having a diameter of 10 μm. The light emitting surface emits light. The light emitting surface having a diameter of 10 μm is produced by attaching a light shielding plate having a pinhole to a light source having a diameter of 10 μm or greater, for example. The pinhole has a diameter of 10 μm. The light shielding plate with the pinhole and the light source are configured so that the light emitting surface of the light source is exposed through the pinhole of the light shielding plate. It is assumed that the light uniformly spreads from the point light source 141 in all directions.

Figure 5:
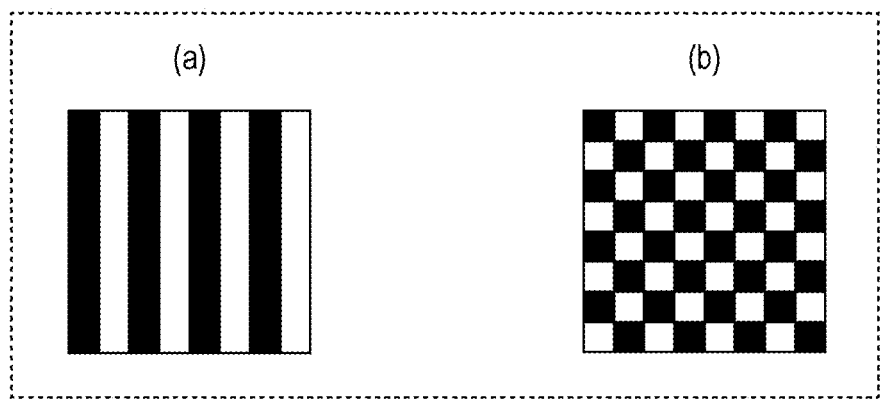
FIG. 5 illustrates examples of a mask according to the first embodiment.

FIG. 5 illustrates an example of the mask 142. More specifically, FIG. 5(a) illustrates an example of a mask 142 having slits, and FIG. 5(b) illustrates an example of a mask 142 having a checker pattern. Note that a black portion in FIG. 5 represents the light-shielding portion described above, and a white portion represents the light-transmitting portion described above. In the example illustrated in FIG. 5, in the slit pattern illustrated in FIG. 5(a), the widths of the light-shielding portions (the black lines) and the widths of the light-transmitting portions (the white lines) are all the same. In addition, in the checker pattern illustrated in FIG. 5(b), the sizes of the light-shielding portions (the black squares) and the sizes of the light-transmitting portions (the white squares) are all the same. Furthermore, the plurality of light-transmitting portions and the plurality of light-shielding portions are set at equal intervals on the mask 142. That is, the plurality of light-transmitting portions and the plurality of light-shielding portions of the mask 142 are periodically and regularly arranged. In addition, the width of the line in the slit pattern or the length of one side of the square in the checker pattern is set such that part of the object becomes bright by the light flux emitted from any one of the point light sources 141 and passing through the mask 142 and the remaining part becomes dark. That is, the above-mentioned width or the length of one side of the square is set so that the bright-and-dark pattern of the light formed on the object and the image sensor 150 by the light flux divides the object into at least two regions (a bright region and a dark region). For example, when the size of the object is 100 µm, the width of the line in the slit pattern or the length of one side of the square of the checker pattern is 30 µm, for example. The mask 142 is produced by, for example, depositing a metal on glass.

Figure 6:
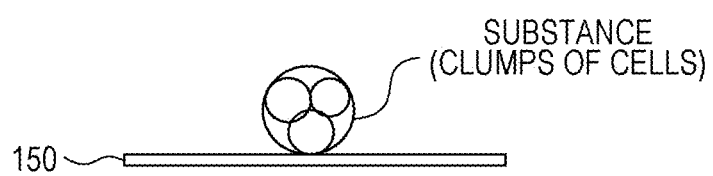
FIG. 6 illustrates an example of an object placed on an image sensor according to the first embodiment.

FIG. 6 illustrates an example of an object placed on the image sensor 150. Note that in FIG. 6, a transparent protective film or the like is not illustrated. An object whose image is to be captured is placed directly on the image sensor 150. The object is, for example, a plurality of translucent substances. A plurality of substances are placed so as to three-dimensionally overlap one another. A specific example of the substance is a cell or a cultured cell. In the example illustrated in FIG. 6, the object is an early embryo.

The image sensor 150 has a plurality of pixels, and the above-described substances are arranged on the image sensor 150. Each of the pixels of the image sensor 150 is disposed on the light receiving surface and acquires the intensity (that is, the brightness value) of the light emitted from the plurality of point light sources 141. The image sensor 150 obtains a captured image on the basis of the intensities of the light acquired by the pixels. That is, when the image sensor 150 is illuminated by the first light source 141A among the plurality of point light sources 141, the image sensor 150 acquires a first image of the substances. When the image sensor 150 is illuminated by the second light source 141B among the plurality of point light sources 141, the image sensor 150 acquires a second image of the substances. In addition, the acquired first image has a plurality of first pixel regions, and the second image has a plurality of second pixel regions. Each of the first pixel regions and the second pixel regions may be one pixel or a block formed from a plurality of pixels. Alternatively, each of the first pixel regions and the second pixel regions may be a region or a point between a plurality of pixels (known as a subpixel).

An example of the image sensor 150 is a complementary metal-oxide semiconductor (CMOS) image sensor or a charge-coupled device (CCD) image sensor.

The plurality of point light sources 141 of the illuminator 140 sequentially emits light. The plurality of point light sources 141 are disposed at different positions and emit light to the object through the mask 142 in different directions.

The control unit 160 controls emission of light from the plurality of point light sources 141 and image capture by the image sensor 150. More specifically, the control unit 160 controls the order in which the plurality of point light sources 141 emit light and the time interval during which the plurality of point light sources 141 emit the light. The control unit 160 is formed from a computer system (not illustrated) including a central processing unit (CPU), a random access memory (RAM), and a read-only memory (ROM). The functions of some or all of the components of the control unit 160 may be achieved by the CPU executing the program stored in the ROM by using the RAM as a work memory. Alternatively, the functions of some or all of the components of the control unit 160 may be achieved by a dedicated hardware circuit.

Figure 7:
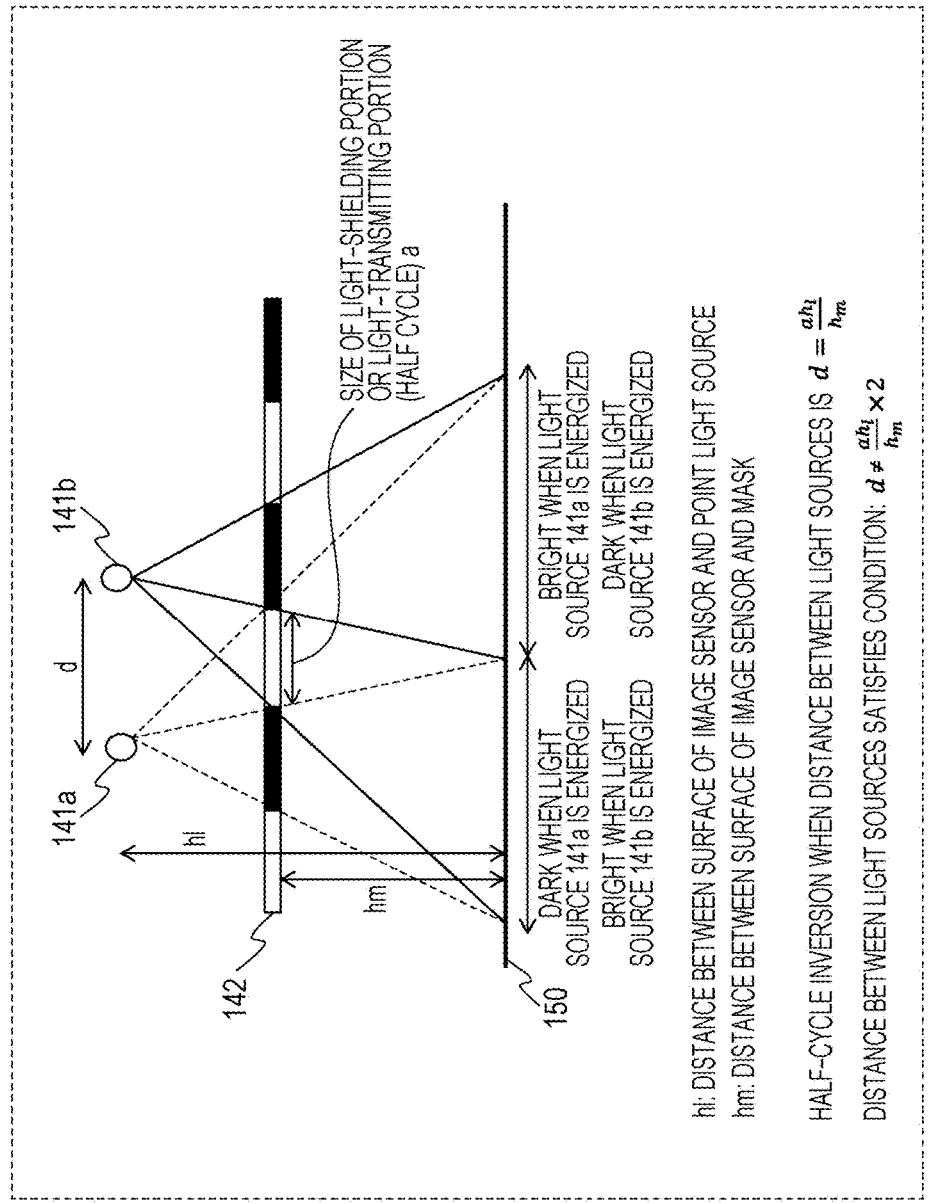
FIG. 7 is a schematic illustration of the interval between the plurality of point light sources according to the first embodiment.

FIG. 7 is a schematic illustration of the interval between the plurality of point light sources 141. In FIG. 7, the length of the light-shielding portion of the mask 142 is "a", and the length of the light-transmitting portion of the mask 142 is "a". In addition, "a" is each of the width of the light-transmitting portion and the width of the light-shielding portion in FIG. 5(a) or each of the length of one side of the light-shielding portion (the black square) and the length of one side of the light-transmitting portion (the white square) of the checker pattern in FIG. 5(b). Note that by sequentially energizing the point light sources 141 one by one, the bright portions and the dark portions on the image sensor 150 move regularly. In other words, the brightness values of the pixels on the image sensor 150 periodically varies so that the pixels change from bright to dark or vice versa. The alternating light-dark cycle at this time is based on the length of the light-shielding portion and the length of the light-transmitting portion of the mask 142 and the interval between the plurality of point light sources 141.

The distance "d" is a distance between the light sources (that is, a distance between the two point light sources 141). In the example illustrated in FIG. 7, the distance d is the distance between the point light source 141a and the point light source 141b included in the plurality of point light sources 141. The distance h1 is the distance from the surface of the image sensor 150 to each of the point light sources 141a and 141b. The distance hm is the distance from the surface of the image sensor 150 to the mask 142. In FIG. 7, the point light source 141a and the point light source 141b are arranged at such positions that the bright-dark pattern on the image sensor 150 can be inverted.

More specifically, in FIG. 7, a dotted line indicate the path in which the light emitted from the point light source 141a passes through the boundary between the light-shielding portion and the light-transmitting portion of the mask 142 and reaches the image sensor 150. In FIG. 7, a solid line indicates a path in which the light emitted from the point light source 141b passes through the boundary between the light-shielding portion and the light-transmitting portion of the mask 142 and reaches the image sensor 150. In the surface of the image sensor 150, the range where the light is blocked by the light-shielding portion of the mask 142 when the point light source 141a is energized becomes a "dark" portion. Subsequently, this range becomes a "bright" portion that receives the light passing through the light-transmitting portion of the mask 142 when the point light source 141b is energized.

When the point light source 141a and the point light source 141b are located at the positions illustrated in FIG. 7, the distance d between the light sources is represented as follows:

$$d = \frac{a h_1}{h_m}. \tag{1}$$

Suppose that the distance d between the light sources satisfies the following Equation (2):

$$d = \frac{a h_1}{h_m} \times 2. \tag{2}$$

Then, even when the plurality of point light sources 141 are sequentially energized one by one, each of the pixels of the image sensor 150 always receives light of the same brightness. For example, one pixel of the image sensor 150 is always located in a "dark" portion, and another pixel is always located in a "bright" portion. In other words, even when the plurality of point light sources 141 are sequentially energized one by one, the "bright" portion and the "dark" portion of the bright-and-dark pattern on the image sensor 150 do not move. Such a state can also be said to be a state in which as viewed from the light receiving surface of the image sensor 150, the arrangement pattern of a plurality of point light sources 141 matches the arrangement pattern of the light-transmitting portions and the light-shielding portions of the mask 142. Therefore, as viewed from the light receiving surface of the image sensor 150, it is necessary to avoid a state in which the arrangement pattern of the point light sources 141 matches the arrangement pattern of the light-transmitting portions and the light-shielding portions of the mask 142. That is, the distance d between the light sources should not satisfy Equation (2). If the distance d between the light sources does not satisfy Equation (2), each of the pixels on the image sensor 150 can periodically receive light having a variety of brightness values ranging from a "bright" level to a "dark" level from the point light sources 141 that are sequentially energized one by one.

Figure 8:
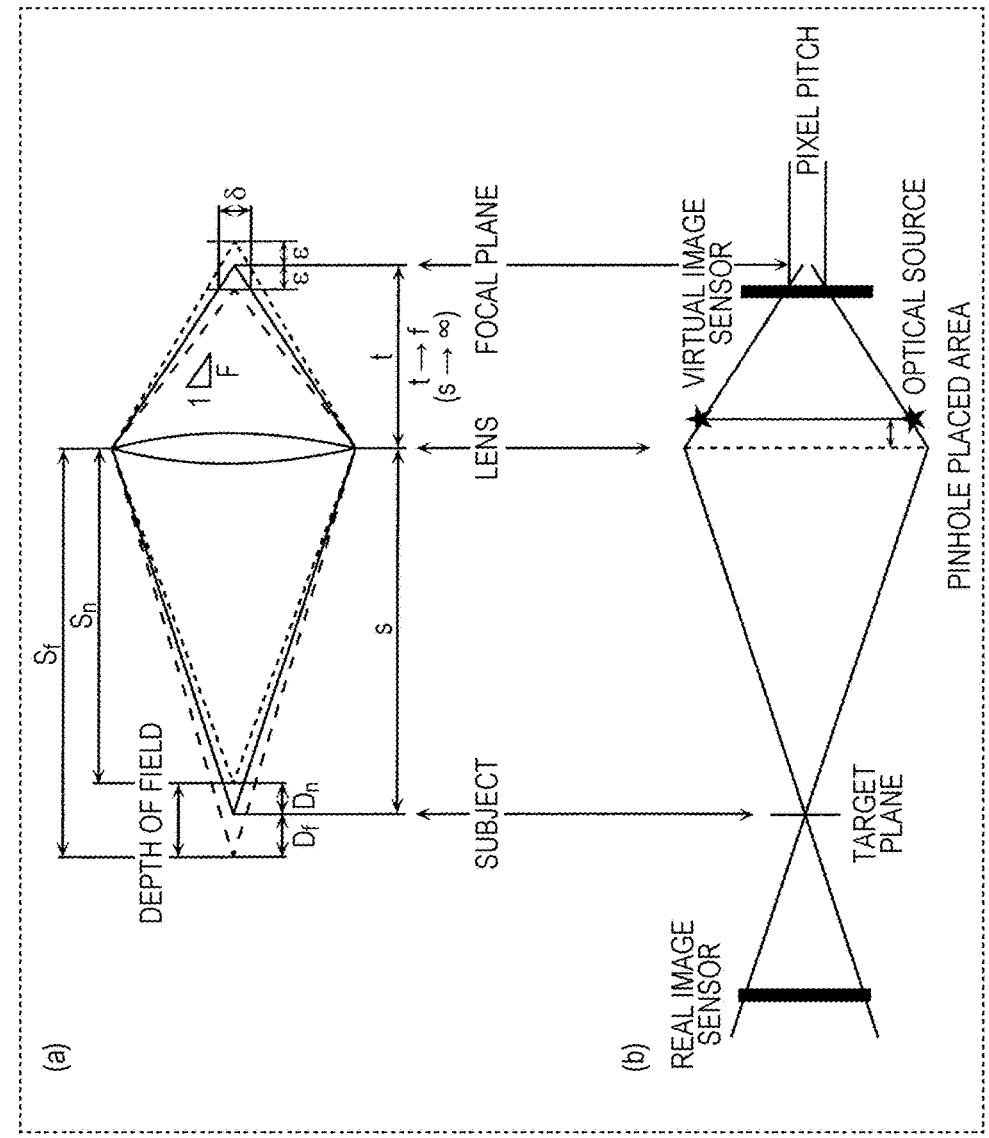
FIG. 8 is a schematic illustration of a range in which the plurality of point light sources are arranged according to the first embodiment.

FIG. 8 is a schematic illustration of a range in which the plurality of point light sources 141 are arranged. More specifically, FIG. 8 is a schematic illustration of the relationship between the focal length of the lens and the depth of field in association with the relationship between the arrangement of the point light sources and the depth of field at the time of refocusing. FIG. 8(*a*) illustrates the relationship between the focal length of the lens and the depth of field, and FIG. 8(*b*) illustrates the relationship between the arrangement of the point light sources and the depth of field at the time of refocusing. Note that the refocusing is described below.

In FIG. 8, "f" represents the focal length of the lens. "s" represents the object distance. "t" represents the distance from the lens to the imaging plane. "F" represents the F value. $\varepsilon$ represents ½ of the depth of focus. $\delta$ represents the diameter of permissible circle of confusion. Sn represents the near point distance. Sf represents the far point distance. Dn represents the front depth of field. Df represents the rear depth of field.

The depth of field when refocusing an image is determined by the width of the distribution range of the illumination positions. In FIG. 8(*b*), the distribution range of the illumination positions indicated by the dotted line corresponding to the lens diameter in FIG. 8(*a*). In the case of the lens illustrated in FIG. 8(*a*), the light reflected by the surface of the subject ("Subject") passes through the lens and forms an image on the focal plane ("Focal Plane"). The depth of field ("Depth of Field") is the sum of the front depth of field Dn and the rear depth of field Df. According to the present disclosure, since refocusing is performed in image capture using transmitted light, the focal plane corresponds to the position of the object in FIG. 8(*a*). In FIG. 8(*b*), the image sensor is located on the left side of the focal plane. According to the present embodiment, although in reality, nothing is located on the right side of the arrangement of point light sources, the actual depth of field can be calculated by setting the pixel pitch of the image sensor as the permissible circle of confusion.

As illustrated in FIG. 8, the range of the illumination position needed to generate the in-focus image on the focal plane corresponds to the size of the lens disposed parallel to the focal plane. In order to observe the object placed at the focal position, the range of the illumination position when for example, a lens diameter of 10 mm of a lens placed at 5 mm away from the object is required is represented by the following circle. That is, the range of the illumination position is represented by a circle with a diameter of 10 mm at the center of which there is the intersecting point of the normal to the focal plane passing through the center of the focal plane and the plane parallel to the focal plane. In addition, the circle is parallel to the focal plane and is located 5 mm away from the focal plane.

1-2 Storage Unit

The storage unit 110 stores the image acquired by the image sensor 150 in association with the position of the point light source 141 (that is, the illumination position) that is illuminated or energized at the time of image capture set by the control unit 160.

FIG. 9 illustrates an example of the information stored in the storage unit 110. The storage unit 110 stores the ID for identifying the image acquired by the image sensor 150 in association with the illumination position of the point light source 141 that is energized at the time of image capture. For example, the illumination position is indicated as a point on the coordinate system with the origin set at the upper left corner of a plane formed from a plurality of effective pixels of the image sensor 150, the x-axis in the lateral direction of the image sensor 150, and the y-axis in the longitudinal direction of the image sensor 150. In the example of the illuminator 140 according to the present embodiment, the plurality of point light sources 141 are disposed on a plane parallel to the surface of the image sensor 150 (that is, the light receiving surface) so as to face the surface of the image sensor 150. That is, the distances from the surface of the image sensor 150 to all of the point light sources 141 are the same. Therefore, the illumination position is expressed in two dimensions. Note that the illumination position may be expressed in three dimensions. In addition, when all of the point light sources 141 are arranged linearly, the illumination position may be expressed in one dimension.

1-3 Focal Plane Input Unit

The focal plane input unit 120 receives specified information indicating a focal plane specified by a user. Alternatively, the focal plane input unit 120 acquires specified information indicating a predetermined focal plane stored in a storage unit (not illustrated).

1-4 Focal Plane Determination Unit

The focal plane determination unit 130 is formed by, for example, a control circuit, a processing circuit, or a processor. The focal plane determination unit 130 determines a virtual focal plane located between the illuminator 140 and the image sensor 150. More specifically, the focal plane determination unit 130 determines the focal plane in accordance with the specified information received by the focal plane input unit 120. Alternatively, the focal plane determination unit 130 may determine the focal plane on the basis of the specified information stored in a storage unit (not illustrated). In other words, the focal plane determination unit 130 acquires information regarding a focal plane located between the image sensor 150 and the mask 142 and having a plurality of focal points.

1-5 Configuration of Integrated Calculation Unit

The integrated calculation unit 170 is formed by at least one control circuit or processing circuit. The integrated calculation unit 170 includes the corresponding point determination unit 171, the coefficient map holding unit 172, the equation generation unit 173, and the calculation unit 174.

The corresponding point determination unit 171 acquires the information regarding the focal plane from the focal plane determination unit 130. Thereafter, for the pixel of the in-focus image on the focal plane determined by the focal plane determination unit 130, the corresponding point determination unit 171 determines, for each of the illumination positions, an intersection point of a straight line extending between a pixel on the in-focus image and the illumination position and the surface of the image sensor 150 as a corresponding point.

The coefficient map holding unit 172 holds a coefficient map.

FIG. 10 illustrates an example of the coefficient map held in the coefficient map holding unit 172.

The coefficient map indicates a coefficient $\alpha$ of the direct light component and the coefficient $\beta$ of the light component other than the direct light component, which are predetermined for a pair consisting of the position of the pixel on the image sensor 150 (that is, the pixel position) and the illumination position, together with the pixel position on the image sensor 150 and the illumination position. In the example illustrated in FIG. 10, the pixel position on the image sensor 150 and the illumination position are expressed by using the coordinates.

Figure 11:
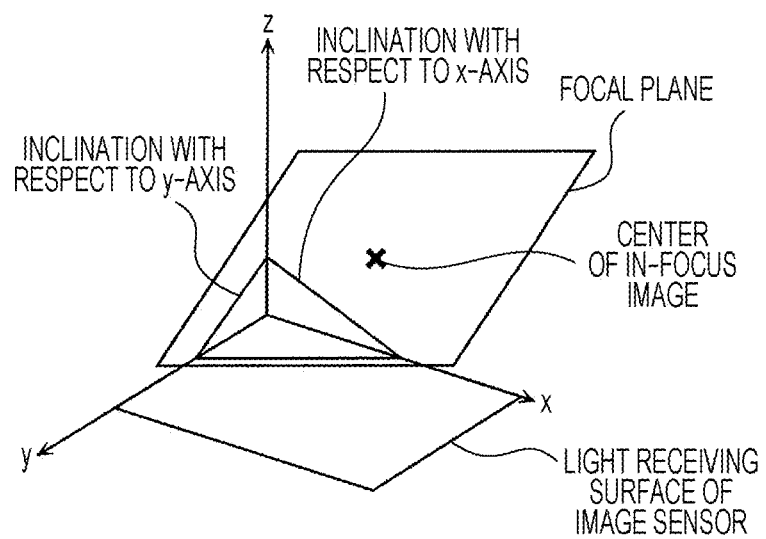
FIG. 11 is a schematic illustration of an example of a focal plane in a coordinate system formed by the x, y, z axes according to the first embodiment.

FIG. 11 is a schematic illustration of an example of a focal plane in a coordinate system with three axes: an x-axis, a y-axis, and a z-axis. The x-axis and the y-axis are located on the surface of the image sensor 150 (that is, the light-receiving surface) and are perpendicular to each other. The z-axis is an axis perpendicular to the x-y plane. The origin of the coordinate system is the position of the pixel located at the upper left corner of the image sensor 150.

The coordinates set forth in the coefficient map indicate a coordinate position in, for example, the coordinate system illustrated in FIG. 11, that is, the coordinate position in a coordinate space. In this example, since the plurality of point light sources 141 are disposed on a plane parallel to the surface of the image sensor 150, the z coordinate values of all of the point light sources 141 are the same. Therefore, in the example of the coefficient map illustrated in FIG. 10, the value of the z coordinate of each of the illumination positions is not set forth. Note that in the example illustrated FIG. 10, the unit of the numerical values of the x-coordinate value and the y-coordinate value of the illumination position is, for example, μm.

For example, each of the coefficients set forth in the coefficient map is determined as follows. That is, the coefficient $\alpha$ of the direct light component is obtained by comparing the result of image capture in the absence of the mask 142 and an object with the result of image capture in the absence of the object but in the presence of the mask 142. Hereinafter, a state in the absence of the mask 142 and the object is referred to as a "maskless state", and a state in the absence of the object but in the presence of the mask 142 is referred to as a "masked state". The maskless state is the same as the state in which the mask 142 has been removed from the measurement system.

The maskless state is defined as a state in which light emitted from a point light source 141i, which is any one of the point light sources 141, reaches the image sensor 150 without being blocked. The brightness value at each of the pixel positions on the image sensor 150 in this state is considered as the maximum value. That is, the maximum value of the brightness detected by the pixel k when the light emitted from the point light source 141i reaches the pixel k on the image sensor 150 is the brightness value obtained at the time of image capture in the maskless state. In the masked state, when the direct light from the point light source 141i passes through the light-transmitting portion of the mask 142 and reaches the pixel k on the image sensor 150, the brightness detected by the pixel k is the same as the above-described maximum value of brightness.

In contrast, in the masked state, when the direct light from a point light source 141n is blocked by the light-shielding portion of the mask 142, the brightness detected by a pixel m is zero. However, in reality, the space above the image sensor 150 can have various transmittance values due to, for example, diffraction. That is, in the masked state, even when the light from the point light source 141n is blocked by the light-shielding portion of the mask 142, the brightness detected by the pixel m does not become zero.

Figure 12:
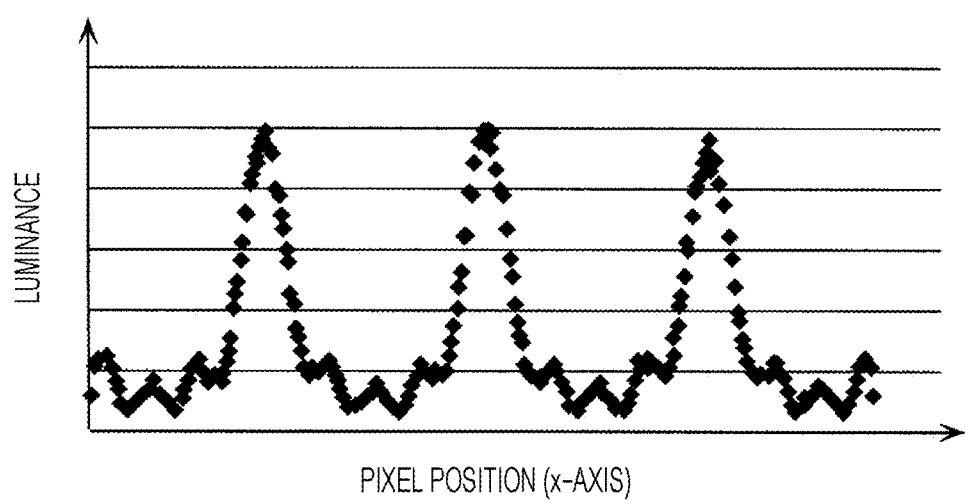
FIG. 12 illustrates an example of the brightness distribution obtained when an image is captured through a slit-pattern mask.

FIG. 12 illustrates an example of the brightness distribution when the image is captured through the slit-pattern mask 142. The image was captured by energizing only one of the point light sources and not energizing the other point light sources. This brightness distribution represents the brightness distribution of a line of pixels in the image sensor 150. More specifically, the brightness distribution is a distribution of brightness recorded for the pixels arranged along the x-axis (the lateral direction) at a specific y coordinate (at a longitudinal position). The brightness values include not only the maximum value and the minimum value but also intermediate values that many pixels have. For example, in FIG. 12, the maximum value indicates a state in which 100 percent of the direct light components are transmitted. The example in FIG. 12 indicates the relationship between the position of a pixel on the image sensor 150 and on the straight line passing through a point immediately beneath the point light source, which is energized at the time of image capture, and the brightness recorded at the pixel position of the pixel. When a pixel on the image sensor 150 is largely away from the point immediately beneath the point light source, the incident angle to the image sensor increases and, thus, the peak of the brightness decreases. However, in the example illustrated in FIG. 12, the distance between the point light source and the surface of the image sensor 150 is sufficiently large with respect to the distance between the pixels, and the brightness values in only an area around the point immediately beneath the point light source are illustrated. Consequently, there is no difference in peak of the brightness among the pixel positions.

For each of the pixels, the ratio of the brightness value obtained in the masked state to the brightness value obtained in the unmasked state is set as the direct light component coefficient $\alpha$ for each of the illumination positions. For example, the direct light component coefficient $\alpha$ is calculated as follows:

(direct light component coefficient $\alpha$ of the pixel i for the point light source j)=(the brightness value detected by the pixel i when the point light source j is energized and the other point light sources are not energized in the masked state)/(the brightness value detected by the pixel i when the point light source j is energized and the other point light sources are not energized in the maskless state).

Note that the direct light component coefficient $\alpha$ may be calculated without capturing an image in the maskless state. Such a technique is described with reference to two examples below.

FIRST EXAMPLE

The plurality of point light sources include a 1st point light source, . . . , a jth point light source, . . . , and an nth point light source, where j is a natural number, n is a natural number, and 1<j≤n. A translucent substance is disposed. An image sensor captures the image of the substance a plurality of times. The image sensor includes a 1st pixel, an ith pixel, . . . and an mth pixel, where i is a natural number, m is a natural number, and 1<i≤m. A mask is located between the image sensor and the plurality of point light sources. When the jth light source is energized and the 1st to nth point light sources other than the jth light source are not energized, the image sensor repeatedly acquires a pixel value L(1j) of the 1st pixel, . . . , a pixel value L(ij) of the jth pixel, . . . and a pixel value L(mj) of the mth pixel for j=1 to n. The processing circuit detects the highest value $L(i)_{max}$ among the pixel values L(i1), . . . , L(ij), . . . , and L(in). Thereafter, the processing circuit repeats the process to determine a direct light component coefficient $E_{ij}$ as $L(ij)/L(i)_{max}$ for i=1 to m and for j=1 to n.

SECOND EXAMPLE

In the first example, after acquiring the pixel values L(i1), . . . , L(ij), . . . , and L(in), the peak (the maximum value) of the pixel value L(ij) when the pixel value L(ij) of the ith pixel are arranged in accordance with the arrangement of the 1st point light source to the nth point light source is identified, and the point light source corresponding to the maximum value is identified. By using the pixel value L(ik) of the ith pixel when the pixels are illuminated by, among the identified point light sources, the point light source k that is the closest to the position immediately above the ith pixel, a process to determine a direct light component coefficient $\alpha_{ij}$ of the pixel i for the point light source j as L(ij)/L(ik) may be performed for i=1 to m and for j=1 to n. Two examples have been described above.

In contrast, for example, according to the present embodiment, the coefficient β of the light component other than the direct light component has a value common to all of the pixels on the image sensor 150 for each of the illumination positions. A light component other than the direct light component is generated as a result of direct light component being refracted and/or scattered by an object, a medium, or the like. Therefore, the amount of light component other than the direct light component depends on the amount of the direct light component. Since the light component other than the direct light component is a component that spreads beyond the pattern of the light-shielding portion and the light-transmitting portion of the mask 142, the amount of light can be considered as the amount of light that reaches the image sensor 150 through the mask 142. Therefore, the light component other than the direct light component of each of the pixels is an amount for one pixel of the amount of the direct light component that reaches the image sensor 150 and is the average of the direct light components of all of the pixels of the image sensor 150 for a particular illumination position. To simplify computation, since the area of the light-shielding portion of the mask 142 is the same as the area of the light-transmitting portion, it is assumed that half the direct light component reaches the image sensor 150, and the coefficient β of the light component other than the direct light component may be set to 0.5.

The equation generation unit 173 acquires the coefficients α and β set forth in the coefficient map. That is, according to the present embodiment, the equation generation unit 173 obtains, for each of the plurality of first pixel regions included in the above-described first image, a ratio α1 of the first light including the direct light directly incident on the image sensor 150 from the first light source 141A and a ratio β1 of the second light including light other than the direct light which is scattered and is incident on the image sensor 150 from the first light source 141A. In addition, the equation generation unit 173 obtains, for each of the plurality of second pixel regions included in the above-described second image, the ratio α2 of third light including direct light directly incident on the image sensor 150 from the second light source 141B and the ratio β2 of fourth light including light other than the direct light which is scattered and is incident on the image sensor 150 from the second light source 141B.

Subsequently, the equation generation unit 173 generates an equation for calculating the brightness of the direct light component and the brightness of the light component other than the direct light component on the specified pixel in the focal plane on the basis of the coefficients α and β set forth in the coefficient map and the brightness of the corresponding point in the captured image stored in the storage unit 110.

The equation is generated on the assumption that the light that has reached the image sensor 150 is formed from the direct light component and the light component other than the direct light component.

That is, the brightness observed at a given point on the image sensor 150 is represented by the sum of the direct light component and the light component other than the direct light component as follows:

$$L_{ij}=a_{ij} \cdot \text{Direct}_{ij}+\beta_j \cdot \text{Global}_{ij} \quad (3)$$

where the direct light component is a component of light that passes through the mask 142, the object, and others and reaches the given point, and the light component other than the direct light component is a component of light that passes through the mask 142 and, thereafter, is refracted and/or scattered by the object and others, and reaches the given point.

In Equation (3), i represents the pixel position on the focal plane or the pixel itself at the pixel position, and j represents the illumination position of the point light source 141 that illuminates the pixel. $L_{ij}$ represents the observed brightness at the corresponding point of the pixel i when the point light source 141 at the illumination position j is energized and the image of the object is captured. $a_{ij}$ is the coefficient of the direct light component corresponding to the illumination position j and the corresponding point of the pixel i. Note that $\alpha_{ij}$ is a known value stored in the coefficient map holding unit 172. $\beta_j$ is the coefficient of the light component other than the direct light component corresponding to the illumination position j. $\beta_j$ is a value common to all of the pixels on the image sensor 150 (that is, the corresponding points). In addition, like $a_{ij}$, $\beta_j$ is a known value stored in the coefficient map holding unit 172.

$\text{Direct}_{ij}$ is a direct light component received by the corresponding point of the pixel i when the point light source 141 at the illumination position j is energized. $\text{Direct}_{ij}$ includes all the information regarding the range that the direct light has transmitted. That is, $\text{Direct}_{ij}$ is a direct light component at all focal points. $\text{Global}_{ij}$ is the light component other than the direct light component received by the corresponding point of the pixel i when the point light source 141 at the illumination position j is energized. $\text{Global}_{ij}$ indicates all of light other than the direct light that reaches the corresponding point of the pixel i.

The brightness observed at the corresponding point of the pixel i can be represented for each of the illumination positions 1 to n as follows:

$$L_{i1} = \alpha_{i1} \cdot Direct_{i1} + \beta_1 \cdot Global_{i1} \quad (4)$$

$$L_{i2} = \alpha_{i2} \cdot Direct_{i2} + \beta_2 \cdot Global_{i2}$$

$$\vdots \quad \vdots \quad \vdots$$

$$\vdots \quad \vdots \quad \vdots$$

$$L_{in} = \alpha_{in} \cdot Direct_{in} + \beta_n \cdot Global_{in}.$$

At this time, what we want to find is the light or the brightness at the pixel position i on the focal plane. The light is formed from the component common to the components $Direct_i 1$ to $Direct_{in}$, that is, the direct light component $Direct_i$ at the pixel position i of the in-focus image on the focal plane and the component common to $Global_i 1$ to $Global_{in}$, that is, a light component $Global_i$ other than direct light component at the pixel position i of the in-focus image on the focal plane. The direct light component $Direct_i$ and the light component $Global_i$ other than direct light component are expressed as follows:

$$Direct_i = \frac{\sum Direct_{ij}}{n} \quad (5)$$

$$Global_i = \frac{\sum Global_{ij}}{n}. \quad (6)$$

However, since $Direct_{i1}$ to $Direct_{in}$ and $Global_{i1}$ to $Global_{in}$ are unknown, it is difficult to directly calculate $Direct_i$ and $Global_i$ from Equations (5) and (6). Therefore, the calculation unit 174 solves the following Equation (7):

$$\begin{bmatrix} L_{i1} \\ L_{i2} \\ \vdots \\ L_{in} \end{bmatrix} = \begin{bmatrix} \alpha_{i1}\beta_1 \\ \alpha_{i2}\beta_2 \\ \vdots \\ \alpha_{in}\beta_n \end{bmatrix} \begin{bmatrix} Direct_i \\ Global_i \end{bmatrix}. \quad (7)$$

The equation generation unit 173 generates the determinant equation (7) described above.

The calculation unit 174 solves the determinant equation (7) generated by the equation generation unit 173 by using the least squares method. In this manner, the calculation unit 174 obtains the brightness of the direct light component and the brightness of the light component other than the direct light component at a pixel on the focal plane.

Since $Direct_i$ and $Global_i$ that satisfy the determinant equation (7) described above are not found, the calculation unit 174 solves the determinant by the least squares method using a pseudo-inverse matrix. To solve the determinant by the least squares method is to find $Direct_i$ and $Global_i$ which minimize a residual error E defined by the following equation (8):

$$E = (Direct_i - Direct_{i1})^2 + (Direct_i - Direct_{i2})^2 + \quad (8)$$

$$\ldots (Direct_i - Direct_{in})^2$$

$$= Direct_i^2 - 2 \cdot Direct_i \cdot Direct_{i1}^2 \ldots + Direct_i^2 -$$

$$2 \cdot Direct_i \cdot Direct_{in} + Direct_{in}^2$$

Hereinafter, for simplicity, the light component Global other than direct light component is removed, and only the direct light component Direct is expressed.

When the residual error E of Equation (8) is minimized, the following equation (9) is satisfied:

$$2(Direct_i - Direct_{i1}) + 2(Direct_i - Direct_{i2}) + \ldots + 2(Direct_i - Direct_{in}) = 0 \quad (9).$$

That is, the following equation (10) is satisfied:

$$Direct_i = \frac{\sum Direct_{ij}}{n}. \quad (10)$$

Equation (10) is the same as Equation (5). The calculation unit 174 solves the determinant equation (7) generated by the equation generation unit 173 by using the least squares method. In this manner, calculation equivalent to the calculation to solve the average of the direct light components of the corresponding points and the average of the light components other than direct light components for each illumination position can be carried out. As a result, the calculation unit 174 can obtain the refocusing result based on the direct light component and the refocusing result based on the light component other than the direct light component for the pixel i.

As described above, according to the present embodiment, the calculation unit 174 obtains the pixel values based on the first and third light corresponding to each of the focal points or the pixel values based on the second and fourth light corresponding to each of the focal points by using the pixel values in the above-described first pixel regions of the first image, the pixel values in the above-described second pixel regions of the second image, the ratio α1 of the first light, the ratio β1 of the second light, the ratio α2 of the third light, and the ratio β2 of the fourth light. Note that the pixel values based on the first light and the third light are the pixel values or brightness values based on the direct light component, and the pixel values based on the second light and the fourth light are the pixel values or brightness values based on the light components other than direct light component.

More specifically, let α1, β1, α2, β2, L1, and L2 be the ratio of the first light, the ratio of the second light, the ratio of the third light, the ratio of the fourth light, the pixel value of the first pixel region, and the pixel value of the second pixel region corresponding to one of a plurality of focal points, respectively. Then, the calculation unit 174 solves the following equation (11) by using the least squares method:

$$\begin{bmatrix} L1 \\ L2 \end{bmatrix} = \begin{bmatrix} \alpha 1 & \beta 1 \\ \alpha 2 & \beta 2 \end{bmatrix} \begin{bmatrix} D \\ G \end{bmatrix}. \quad (11)$$

As a result, the calculation unit 174 obtains a pixel value D based on the first light and the third light corresponding to the above-described one of the focal points and a pixel value G based on the second light and the fourth light corresponding to the one of the focal points.

The image generation unit 190 is formed form at least one control circuit, processing circuit, or processor. The image generation unit 190 generates an in-focus image by using the refocusing result based on the direct light component generated by the image generation unit 190 and generates an in-focus image by using the refocusing result based on light components other than the direct light component. Hereinafter, the in-focus image generated by the refocusing result based on the direct light component is also referred to as an "image of a direct light component", an "in-focus image of a direct light component", or an "in-focus image by a direct light component". An in-focus image generated by a result of refocusing by a light component other than the direct light component is also referred to as an "image of a light component other than the direct light component", an "in-focus image based on a light component other than the direct light component", or an "in-focus image by a light component other than the direct light component".

As described above, according to the present embodiment, by using the pixel values based on the above-described first light and third light or the pixel values of the above-described second light and fourth light corresponding to each of the focal points, the image generation unit 190 generates a cross-sectional image of the substance on a focal plane. The cross-sectional image generated by using the pixel values based on the first light and the third light is an image based on the direct light components, and the cross-sectional image generated by using the pixel values of the second light and the fourth light Is an image based on the light components other than direct light components.

1-6 Image Output Unit

The image output unit 200 displays the generated image of the direct light component and the generated image of the light component other than the direct light component. Alternatively, the image output unit 200 externally outputs the generated images. To display the images, the image output unit 200 includes, for example, a display. To externally output the images, the image output unit 200 includes, for example, a USB connector.

1-7 Operation Performed by Image Generation Apparatus

The operation performed by the image generation apparatus 10 having the configuration described above is described below.

Figure 13:
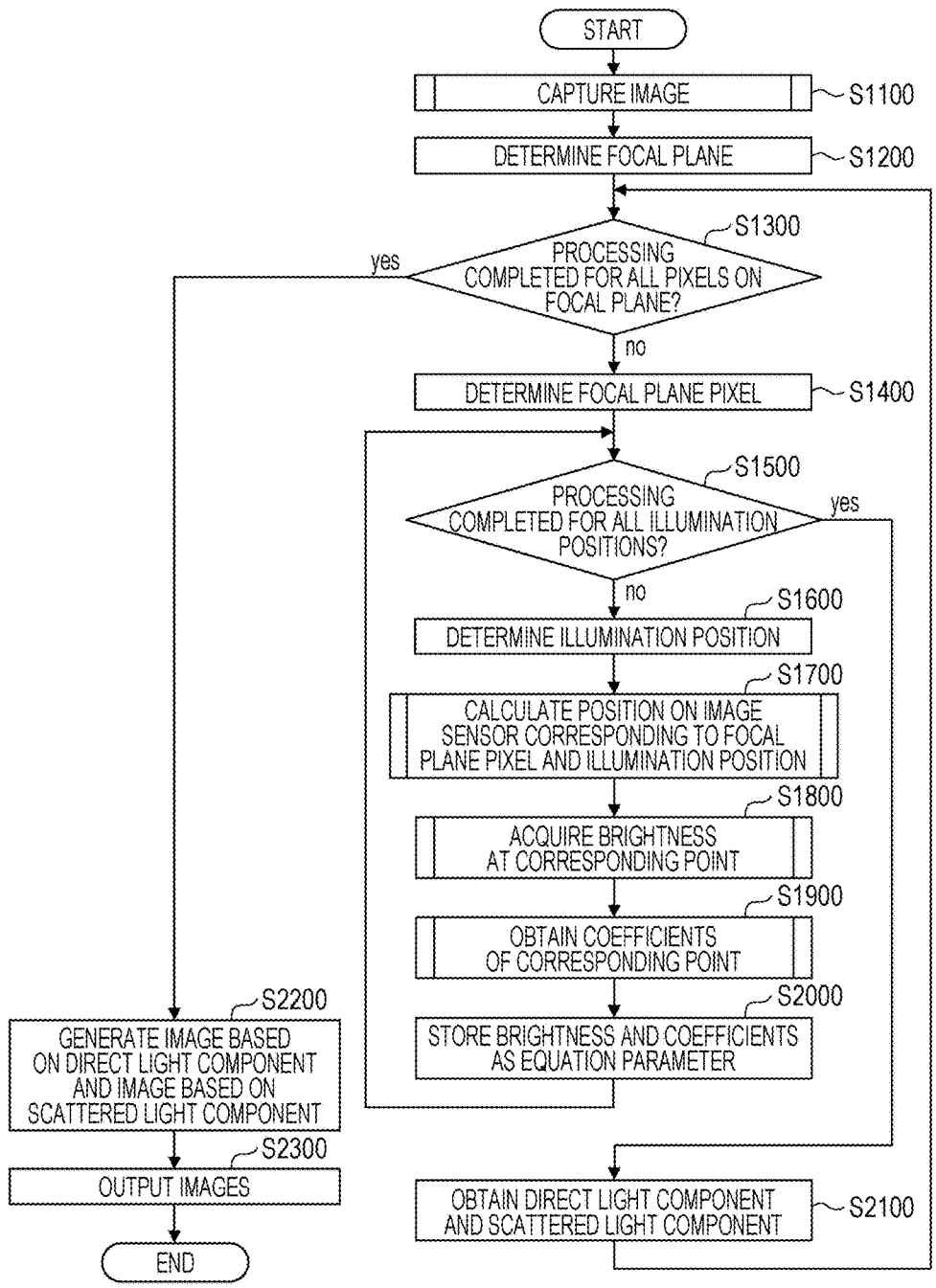
FIG. 13 is a flowchart illustrating an example of the operation performed by the image generation apparatus according to the first embodiment.

FIG. 13 is a flowchart illustrating an example of the operation performed by the image generation apparatus 10 according to the first embodiment.

Step S1100

The image capturing unit 100 sequentially uses the plurality of point light sources 141 of the illuminator 140 to illuminate the object with the light passing through the mask 142 and captures a plurality of images of the object. More specifically, the image capturing unit 100 records the intensity of the light that reaches the light receiving surface of the image sensor 150 each time one of the point light sources 141 of the illuminator 140 emits the light to the object. In this manner, the image capturing unit 100 obtains the images of the object. Each of the obtained images is stored in the storage unit 110 together with the position information of the point light source 141 that emits light to the object to capture the image (that is, the illumination position). In this case, the positions of the plurality of point light sources 141 are fixed with respect to the image sensor 150, and the position information of each of the plurality of point light sources 141 is predetermined. The image capturing process in step S1100 is described in more detail below.

Step S1200

The focal plane determination unit 130 obtains the specified focal plane information from the focal plane input unit 120. The specified focal plane information includes, but not limited to, the coordinate values of the center of the focal plane and the value indicating the inclination of the focal plane. As illustrated in FIG. 11, the inclination of the focal plane is defined as the angle formed by the intersection line of the focal plane and the xz plane and the x-axis, for example. In addition, for example, the inclination of the focal plane is defined as the angle formed by the intersection line of the focal plane and the yz plane and the y-axis. The coordinate values of the center of the focal plane are the coordinate values of the point on the focal plane corresponding to the pixel at the center of the in-focus image.

Step S1300

The corresponding point determination unit 171 refers to a list of pixels of a predetermined in-focus image on the focal plane (hereinafter referred to as a "generated pixel list") and determines whether determination of the corresponding point is completed for all of the pixels included in the in-focus image.

If determination of corresponding points of all the pixels included in the generated pixel list has been completed (yes in step S1300), the processing proceeds to step S2400. However, if the determination of the corresponding point of any one of the pixels in the generated pixel list has not been completed (no in step S1300), the processing proceeds to step S1400.

Step S1400

The corresponding point determination unit 171 selects, from among the pixels included in the generated pixel list, a pixel for which a corresponding point has not yet been determined. In this manner, the pixels (that is, the focal plane pixels) are determined. Note that these pixels are also referred to as "selected pixels". Each of the pixels in the generated pixel list is identified by, for example, a number assigned to the pixel. Alternatively, for example, each of the pixels is identified by the coordinate values on the xy plane having an origin at the upper left corner pixel of the in-focus image to be generated. Selection of pixels in the generated pixel list is performed in ascending order, for example.

Step S1500

The corresponding point determination unit 171 refers to a predetermined list of the illumination positions (hereinafter referred to as an "illumination list") and determines whether determination of corresponding points has been completed for all of the illumination positions.

If the determination of corresponding points has been completed for all of the illumination positions included in the illumination list (yes in step S1500), the processing proceeds to step S2300. However, if the determination of the corresponding point for any one of the illumination positions in the illumination list has not been completed (no in step S1500), the processing proceeds to step S1600.

Step S1600

The corresponding point determination unit 171 selects, from among the plurality of illumination positions included in the illumination list, an illumination position for which a corresponding point has not yet been determined. In this manner, the illumination position is determined. Each of the illumination positions in the illumination list is identified by, for example, a number assigned to the illumination position. Alternatively, for example, each of the illumination positions is identified by coordinate values in a coordinate system formed by an xy plane that is the surface of the image sensor 150 and the z-axis orthogonal to the xy plane. The selection of the illumination position in the illumination list is performed in ascending order, for example.

Step S1700

The corresponding point determination unit 171 obtains, as the corresponding point, the intersection point of the straight line extending between the illumination position determined in step S1600 and the pixel position on the in-focus image to be generated which is determined in step S1400 and the surface of the image sensor 150. In this manner, the corresponding point for the illumination position and the pixel is determined. The calculation of the position of the corresponding point is described in more detail below.

Step S1800

The equation generation unit 173 acquires, from the storage unit 110, the captured image corresponding to the illumination position determined in step S1600, that is, the image captured when the point light source 141 at the illumination position is energized. Thereafter, the equation generation unit 173 obtains, from the acquired captured image, the brightness value at the position of the corresponding point determined in step S1700. A technique for obtaining the brightness value is described in more detail below.

Step S1900

The equation generation unit 173 acquires the coefficients corresponding to the illumination position determined in step S1600 and the corresponding point determined in step S1700. That is, the equation generation unit 173 refers to the coefficient map stored in the coefficient map holding unit 172 and acquires the coefficients α and β associated with the illumination position and the corresponding point (that is, the pixel position on the image sensor 150). A technique for acquiring the coefficients is described in more detail below.

Step S2000

The equation generation unit 173 stores, as the equation parameters, the brightness value at the corresponding point acquired in step S1800 and the coefficients α and β acquired in step S1900. Subsequently, the processing in steps S1500 to S2000 is repeated. In this manner, the equation generation unit 173 collects the parameters necessary for a determinant used to solve each of the direct light component $Direct_i$ and the light component $Global_i$ other than the direct light component for the pixel on the focal plane selected in step S1400. As a result, the determinant is generated.

Step S2100

The calculation unit 174 solves the determinant generated by the equation generation unit 173 by using the least squares method. Subsequently, the processing in steps S1300 to S2100 is repeated. In this manner, for each of all of the pixels on the focal plane, the brightness (or brightness value) of each of the direct light component $Direct_i$ and the light component $Global_i$ other than direct light component at the position of the pixel can be obtained.

Step S2200

The image generation unit 190 generates the in-focus image of the direct light components on the focal plane and the in-focus image of the light components other than the direct light components on the basis of the brightness values of the direct light components calculated for all of the pixels and the brightness values of the light components other than the direct light components on the focal plane.

Step S2300

The image output unit 200 outputs the images generated in step S2200. When the image output unit 200 is a display, the in-focus image of the direct light components generated in step S2200 and the in-focus image of the light components other than the direct light components are displayed.

Figure 14:
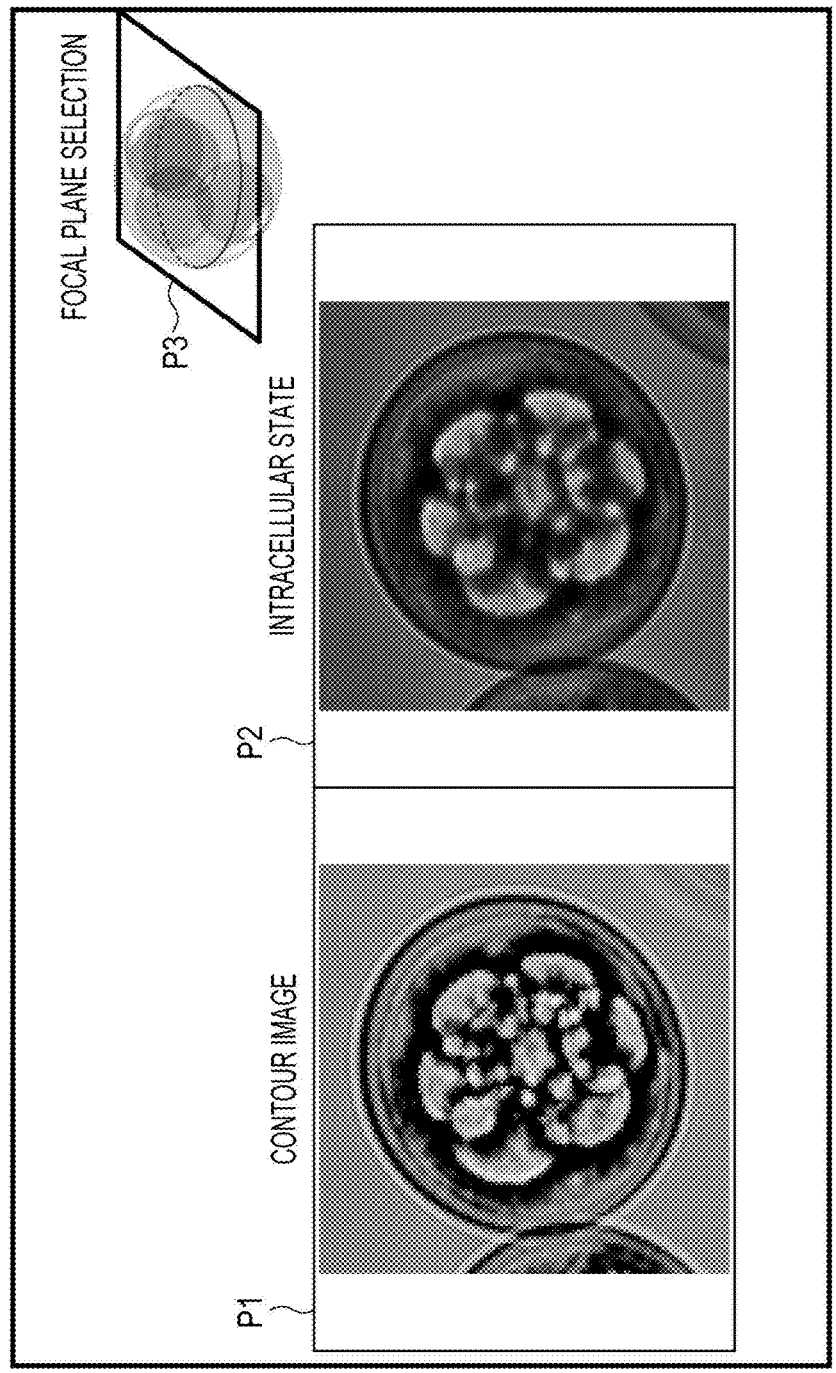
FIG. 14 illustrates an example of in-focus images displayed by an image output unit according to the first embodiment.

FIG. 14 illustrates an example of the in-focus image displayed by the image output unit 200. For example, an in-focus image P1 of the direct light components is displayed in the form of a "contour image" on the left side, and an in-focus image P2 of the light components other than direct light components is displayed in the form of an "intracellular state" on the right side. In addition, on the upper right of the in-focus images P1 and P2, a schematic illustration of the selected focal plane P3 is displayed, for example. The focal plane input unit 120 is a pointing device, such as a mouse. The focal plane input unit 120 rotates or moves the object and the focal plane P3 appearing in the schematic illustration in accordance with the operation performed by the user. Thus, the focal plane P3 can be adjusted.

1-8 Image Capturing Process

The operation performed by the image capturing unit 100 (that is, the image capturing process) in step S1100 is described in detail below.

Figure 15:
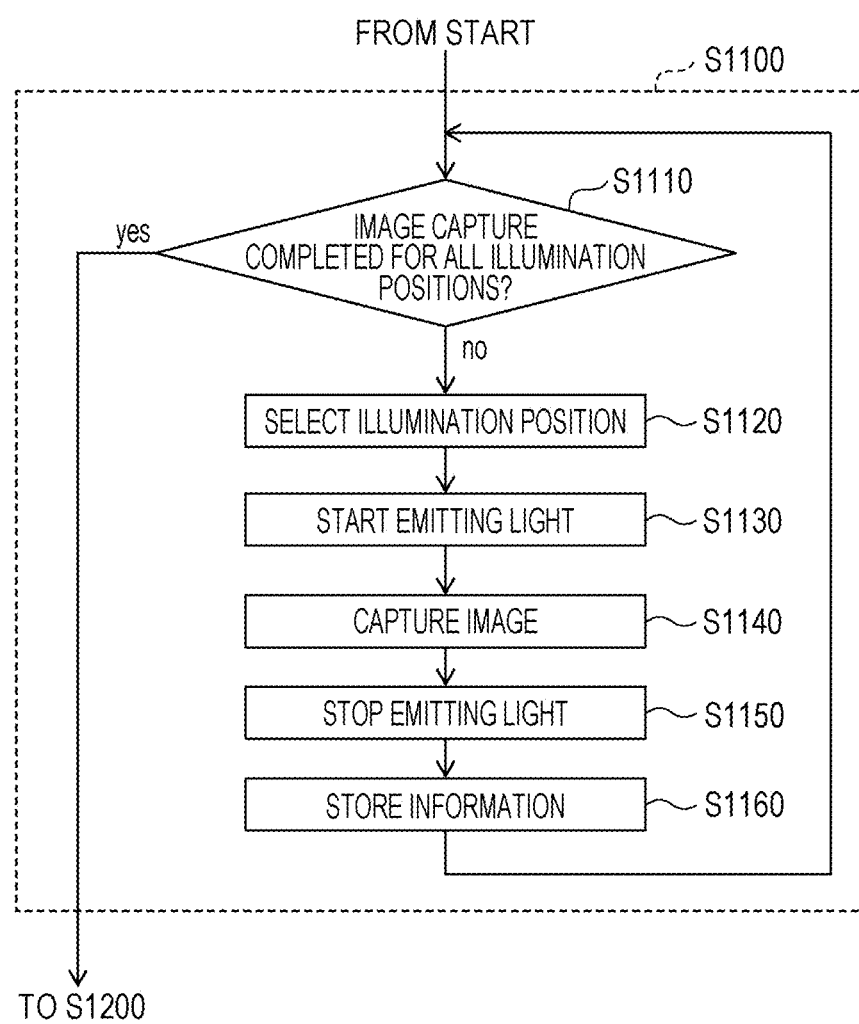
FIG. 15 is a flowchart illustrating an example of the operation performed by an image capturing unit according to the first embodiment.

FIG. 15 is a flowchart illustrating an example of the operation performed by the image capturing unit 100.

Step S1110

The control unit 160 refers to the list of predetermined illumination positions or the illumination positions specified by an external input (not illustrated) (hereinafter, the list is referred to as an illumination position list). Thereafter, for each of all of the illumination positions included in the illumination position list, the control unit 160 determines whether image capture of the object which is illuminated by the point light source 141 located at the illumination position has ended.

If image capture by using illumination from the point light sources 141 located at all the illumination positions included in the illumination position list has been completed (yes in step S1110), the processing proceeds to step S1200. However, if image capture by using illumination from the point light source 141 at any one of the illumination positions in the illumination position list has not yet ended (no in step S1110), the processing proceeds to step S1120.

Step S1120

The control unit 160 selects, from among the plurality of illumination positions included in the illumination position list, the one from which illumination has not yet been produced and outputs a control signal to the illuminator 140. In the illumination position list, each of the illumination positions is identified by, for example, a number assigned to the illumination position. Alternatively, each of the illumination positions is identified by coordinate values in the coordinate system (that is, the xyz space) illustrated in FIG. 11, for example. The selection of the illumination position in the illumination position list is performed, for example, in ascending order.

Step S1130

The illuminator 140 starts emitting light to the object in accordance with the control signal output from the control unit 160 in step S1120. That is, the point light source 141 located at the illumination position selected in step S1120 starts emitting light.

Step S1140

While the object is being illuminated by the point light source 141, the image sensor 150 obtains an image formed by the light that is emitted from the point light sources 141 and that passes through the mask 142 and transmits the object and the light that is refracted and/or scattered by the object (that is, the image sensor 150 obtains a captured image).

Step S1150

Subsequently, the control unit 160 outputs a control signal to the illuminator 140 to stop emitting light to the object. Note that the emission of light does not necessarily have to be stopped in response to a control signal from the control unit 160. For example, the illuminator 140 may count the time length from the start of emitting light and may actively stop emitting light when the measured time length exceeds a predetermined time length. Alternatively, after the image sensor 150 completes acquiring the image in step S1140, the image sensor 150 may output, to the illuminator 140, a control signal to stop emitting light.

Step S1160

Subsequently, the control unit 160 outputs, to the storage unit 110, the image acquired in step S1140 and the position information of the point light source 141 (that is, the illumination position) used for illumination in step S1130. Thereafter, as illustrated in FIG. 9, the storage unit 110 stores the image in association with the illumination position. After step S1160, the processing returns to step S1110.

By repeating the processing from step S1110 to step S1160, light is sequentially emitted to the object from each of the point light sources 141 located at all of the illumination positions included in the illumination position list. Each time light is emitted onto the object, an image is acquired as a captured image.

1-9 Corresponding Point Determination Process

Figure 16:
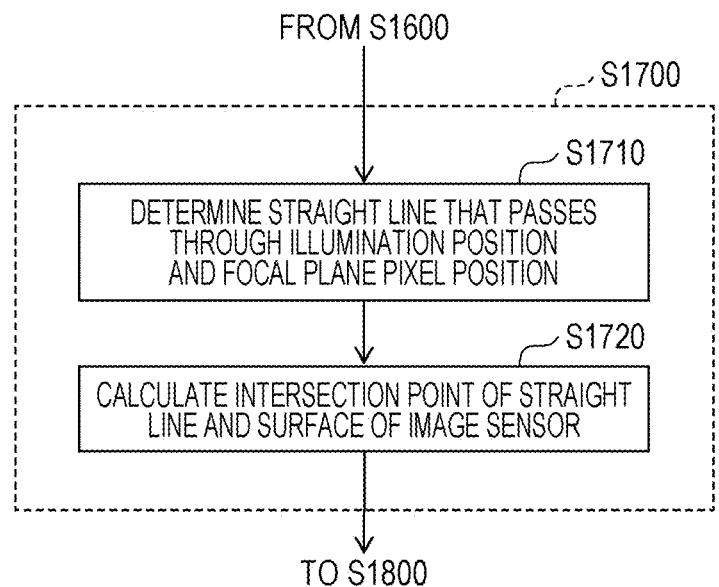
FIG. 16 is a flowchart illustrating the detailed operation performed by a corresponding point determination unit according to the first embodiment.

FIG. 16 is a flowchart illustrating the operation performed by the corresponding point determination unit 171 in step S1700 in detail. The operation performed by the corresponding point determination unit 171 in step S1700 is described in detail below.

Step S1710

The corresponding point determination unit 171 obtains a straight line passing through the selected illumination position and the position of the selected pixel on the focal plane (that is, the focal plane pixel).

Figure 17:
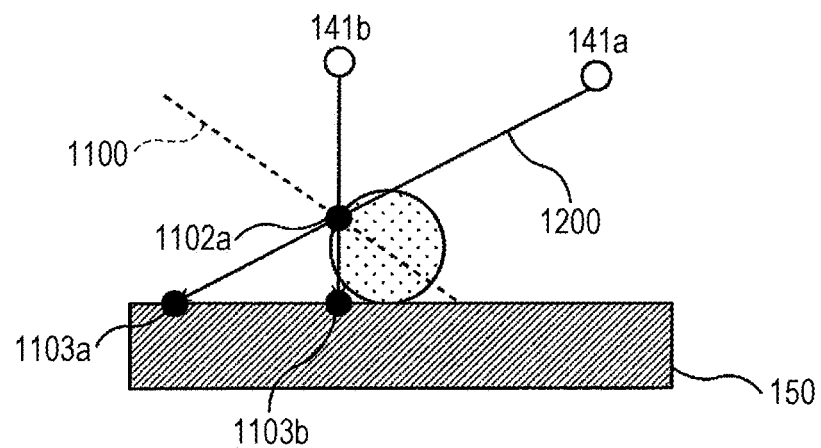
FIG. 17 illustrates the relationship among the plurality of point light sources, a selected pixel, and corresponding points according to the first embodiment.

FIG. 17 illustrates the relationship among a plurality of point light sources 141, the selected pixel, and the corresponding points. The corresponding point determination unit 171 finds a straight line 1200 passing through the illumination position of the point light source 141a, which is one of the plurality of point light sources 141 illustrated in FIGS. 3 and 4, and a selected pixel 1102a on the focal plane 1100 (that is, the focal plane pixel).

Step S1720

The corresponding point determination unit 171 obtains a point at which the straight line obtained in step S1710 intersects with the surface of the image sensor 150 (that is, the light receiving surface). The obtained point is the corresponding point. In the example illustrated in FIG. 17, the corresponding point determination unit 171 obtains, as a corresponding point, a point 1103a at which the straight line 1200 passing through the illumination position of the point light source 141a and the focal plane pixel 1102a intersects with the surface of the image sensor 150. In this manner, the corresponding point 1103a is determined for the illumination position of the point light source 141a and the focal plane pixel (or the selected pixel) 1102a. Note that in step S1710, when a straight line 1200 passing through the illumination position of the point light source 141b and the focal plane pixel 1102a is obtained, the corresponding point determination unit 171 obtains a corresponding point 1103b. That is, the corresponding point determination unit 171 obtains, as a corresponding point, a point 1103b at which a straight line passing through the illumination position of the point light source 141b and the focal plane pixel 1102a intersects with the surface of the image sensor 150. In this manner, the corresponding point 1103b is determined for the illumination position of the point light source 141b and the focal plane pixel (or the selected pixel) 1102a. The corresponding point on the light receiving surface of the image sensor 150 is represented by the coordinate values on the xy plane illustrated in FIG. 11, for example.

1-10 Acquisition of Brightness of Corresponding Point

Figure 18:
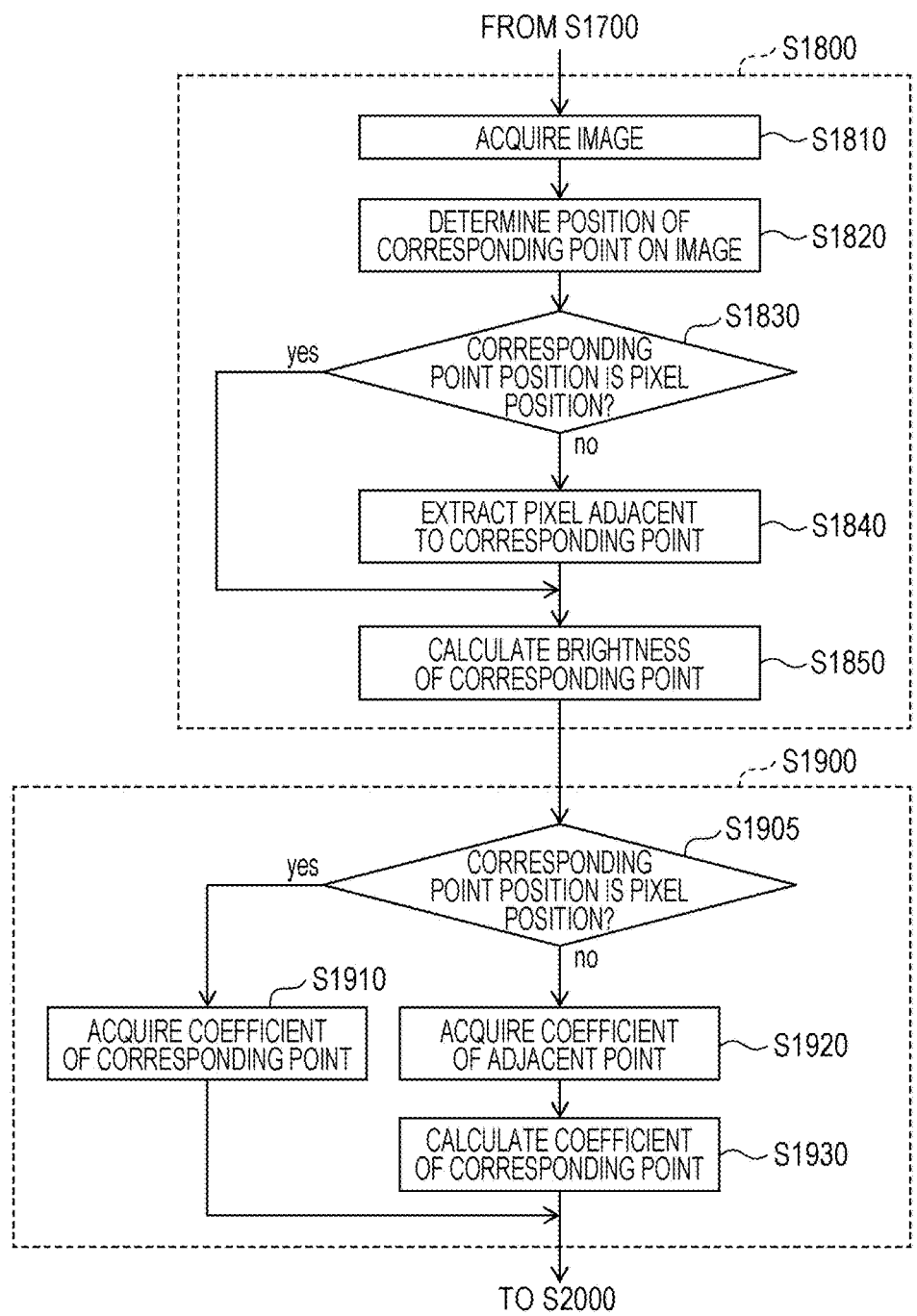
FIG. 18 is a flowchart illustrating the detailed operation performed by an equation generation unit according to the first embodiment.

FIG. 18 is a flowchart illustrating the operation performed by the equation generation unit 173 in steps S1800 and S1900 in detail.

Step S1810

The equation generation unit 173 acquires, from the storage unit 110, the image captured using the point light source 141a at the illumination position determined in step S1600.

Step S1820

The equation generation unit 173 determines the position of the corresponding point calculated in step S1700 in the captured image on the image sensor 150. More specifically, the equation generation unit 173 determines the position of the corresponding point in the captured image on the basis of the arrangement of the pixels included in the captured image.

Step S1830

The equation generation unit 173 determines whether the position of the corresponding point in the captured image determined in step S1820 is the same as the pixel position on the captured image acquired in step S1810.

If the position of the corresponding point is the same as the pixel position on the captured image (yes in step S1830), the processing proceeds to step S1850. However, if the position of the corresponding point is not the same as the pixel position on the captured image (no in step S1830), the processing proceeds to step S1840.

Step S1840

The equation generation unit 173 identifies or extracts a plurality of pixels closest to the corresponding point (these pixels are also referred to as "adjacent pixels").

Step S1850

If the position of the corresponding point in the captured image is the same as any one of the pixel positions in the captured image acquired in step S1810, the equation generation unit 173 adopts the brightness at the pixel position as the brightness of the corresponding point. However, if the position of the corresponding point in the captured image is an intermediate position between the plurality of pixels, the equation generation unit 173 performs interpolation processing using the brightness values of a plurality of pixels (for example, four pixels) around the corresponding point and calculates the brightness value of the corresponding point in the captured image. More specifically, for example, the equation generation unit 173 obtains the distance between each of a plurality of pixels closest to the corresponding point (for example, four adjacent pixels) and the corresponding point. Thereafter, the equation generation unit 173 multiplies a ratio of the distance between the corresponding point and each of the pixels to the sum of the distances by the brightness value of the pixel and sums the calculated values. Thus, the equation generation unit 173 obtains the brightness value of the corresponding point in the captured image.

Figure 19:
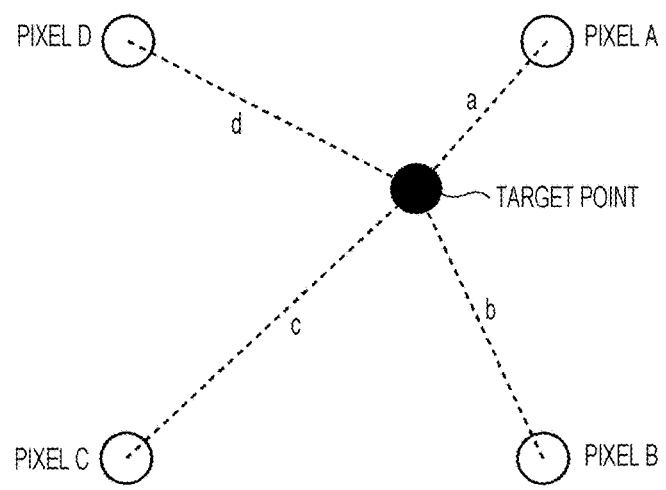
FIG. 19 is a schematic illustration of calculation of the brightness value of a corresponding point according to the first embodiment.

FIG. 19 is a schematic illustration of the calculation of the brightness value of the corresponding point carried out in step S1850. In FIG. 19, let a, b, c, and d denote the distances between each of the four pixels A to D surrounding the corresponding point and the corresponding point, respectively. Then, the brightness value $L_t$ of the corresponding point is calculated as follows:

$$L_t = \left(\frac{L_a}{a} + \frac{L_b}{b} + \frac{L_c}{c} + \frac{L_d}{d}\right) \times (a+b+c+d) \div 16 \quad (12)$$

where $L_a$, $L_b$, $L_c$, and $L_d$ are the brightness values of the pixels A, B, C, and D, respectively.

1-11 Acquisition of Coefficient of Corresponding Point

The equation generation unit 173 acquires the brightness of the corresponding point in step S1800 and further acquires the coefficient α of the direct light component and the coefficient β of the light component other than direct light component at the corresponding point in step S1900.

Step S1905

In step S1905, the equation generation unit 173 determines whether the position of the corresponding point in the determined captured image is the same as the pixel position in the captured image acquired in step S1810.

Step S1910

If, in step S1905, the position of the corresponding point in the captured image is the same as the position of any one of the pixels of the captured image, the equation generation unit 173 acquires, from the coefficient map, the coefficients α and β corresponding to the position of the pixel. That is, the equation generation unit 173 acquires, from the coefficient map, the coefficient α of the direct light component and the coefficient β of the light component other than the direct light component corresponding to the position of the pixel and the illumination position determined in the immediately preceding step S1600. Thereafter, the processing proceeds to step S2000.

Step S1920

If, in step S1905, the position of the corresponding point in the captured image is located between the plurality of pixels of the captured image (no in step S1905), the equation generation unit 173 acquires, from the coefficient map, the coefficients α and β corresponding to the position of each of the above-described plurality of adjacent pixels of the corresponding point (these positions are also referred to as "adjacent points"). That is, for each of the plurality of adjacent pixels for the corresponding point extracted in step S1840, the equation generation unit 173 acquires, from the coefficient map, the coefficient α of the direct light component and the coefficient β of the light component other than the direct light component corresponding to the pixel position and the illumination position of the adjacent pixel.

Step S1930

The equation generation unit 173 performs interpolation processing on each of the coefficient α of the direct light component and the coefficient β of the light component other than direct light component of each of the adjacent pixels of the corresponding point acquired in step S1920. In this manner, the equation generation unit 173 determines the coefficient α of the direct light component and the coefficient β of the light component other than direct light component at the corresponding point. The interpolation processing technique is the same as in the case of the brightness in step S1850. That is, the equation generation unit 173 obtains the distance between the corresponding point and each of the adjacent pixels and, multiplies the coefficient of each pixel by the ratio of the distance between the corresponding point and each adjacent pixel, and sums the calculated values. Thus, the equation generation unit 173 obtains the coefficients α and β of the corresponding point.

Effect

As described above, according to the image generation apparatus 10 according to the first embodiment, light is emitted from a plurality of point light sources 141 located at different positions onto an object and the image sensor 150 through the mask 142 having a repeating pattern of a light-shielding portion and a light-transmitting portion, such as a slit pattern or a checkered pattern. Thereafter, the image generation apparatus 10 captures the image of the object illuminated by the transmitted light, which is the light transmitted through the mask 142. In addition, the image generation apparatus 10 can generate two types of in-focus images on a freely selected focal plane by performing Operations 1) to 4) described below on each of the pixels of the image acquired by the image capture. The two types of in-focus images are an in-focus image based on a direct light component and an in-focus image based on a light component other than the direct light component.

The above-mentioned operations are as follows:
1) Determining a focal plane.
2) Finding a corresponding point of the position of each of the focal plane pixels for each of the illumination positions.
3) Determining the observed brightness, the coefficient of the direct light component, and the coefficient of the light component other than the direct light component at the corresponding point, and generating a determinant whose terms are the direct light component and the light component other than the direct light component of the light at the position of the focal plane pixel.
4) Finding the direct light component and the light component other than direct light component at the position of the focal plane pixel by using the least squares method.

In the in-focus image obtained on the basis of the direct light component through the above procedure, the boundary surface, that is, the contour lines of the object at the focal plane can be made clear. Furthermore, in the in-focus image based on the light component other than the direct light component, a region including the scattering substance of the object in the focal plane can be made clear. For example, when the object is an early embryo, the boundary surface due to the embryonic membrane and the cell membrane becomes clear in the in-focus image based on the direct light component. In contrast, in the in-focus image based on the light component other than direct light component, the position and region in which the cell is located become clear.

Furthermore, it is possible to perform separation of the direct light component from the light component other than the direct light component and refocusing calculation at the same time and obtain the direct light component and the light component other than the direct light component by using all of the information regarding the acquired image. Consequently, it is possible to acquire an image based on the direct light component and an image based on the light component other than the direct light component without deteriorating the depth of field set by the arrangement of the illumination light sources.

Second Embodiment

Figure 20:
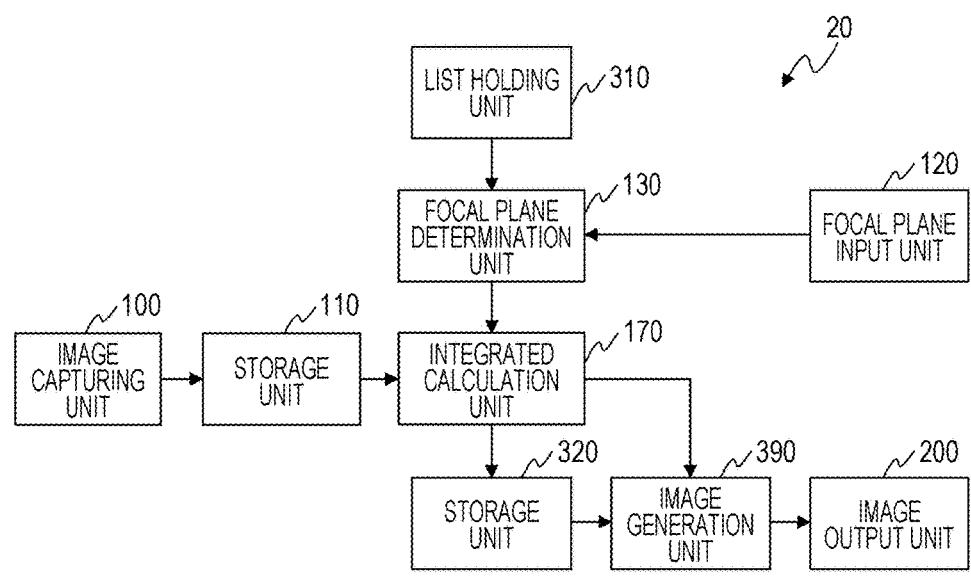
FIG. 20 is a functional block diagram of an image generation apparatus according to a second embodiment.

3DCG Generation from Light Component other than Direct Light Component 2 Configuration of Image Generation Apparatus FIG. 20 is a functional block diagram of an image generation apparatus 20 according to the second embodiment.

As illustrated in FIG. 20, the image generation apparatus 20 includes an image capturing unit 100, a storage unit 110, a list holding unit 310, a focal plane input unit 120, a focal plane determination unit 130, an integrated calculation unit 170, a storage unit 320, an image generation unit 390, and an image output unit 200.

That is, as compared with the image generation apparatus 10 according to the first embodiment illustrated in FIG. 2, the image generation apparatus 20 further includes the list holding unit 310 and the storage unit 320 and includes the image generation unit 390 instead of the image generation unit 190. The other constituent elements of the image generation apparatus 20 are the same as those of the image generation apparatus 10 according to the first embodiment. Accordingly, detailed description of the same constituent elements is not repeated as appropriate.

Since the configuration of the image capturing unit 100 is the same as that illustrated in FIG. 1 or 2, description of the image capturing unit 100 is not repeated.

2-1 List Holding Unit

The list holding unit 310 holds a horizontal focal plane list. The horizontal focal plane list has, as horizontal focal planes, a plurality of planes that are parallel to the surface of the image sensor 150 and that have different z-axis values in a coordinate system illustrated in FIG. 11. More specifically, the horizontal focal plane list has, for example, the value of the z-axis as a parameter for specifying a horizontal focal plane. The horizontal focal plane is used to generate a three-dimensional brightness distribution which is basic data for 3-Dimensional Computer Graphics (3DCG) generation. Therefore, the range of the values of the z-axis in the horizontal focal plane list corresponds to the range for generating 3DCG. For example, if the object is a substance having a diameter of about 100 µm the range of the value of the z-axis set forth in the horizontal focal plane list is 1 µm to 100 µm, and the interval of the planes set forth in the horizontal focal plane list is 1 µm.

According to the second embodiment, the horizontal focal plane list indicates a plane that is horizontal to the surface of the image sensor 150 as a focal plane. However, if the horizontal focal plane list indicates the number of focal planes and the arrangement of the focal planes that are sufficient to calculate the brightness at each of points in the three-dimensional coordinate space, the horizontal focal plane list may indicate a plane other than the plane parallel to the image sensor 150.

The configuration of the integrated calculation unit 170 is the same as that illustrated in FIG. 1 or 2. Accordingly, description of the integrated calculation unit 170 is not repeated.

2-2 Storage Unit

The storage unit 320 stores the brightness in the three-dimensional coordinate space obtained from the in-focus image based on the light component other than the direct light component. That is, the storage unit 320 stores the brightness of the light component other than the direct light component at each of a plurality of coordinate positions in the three-dimensional coordinate space.

Figure 21:
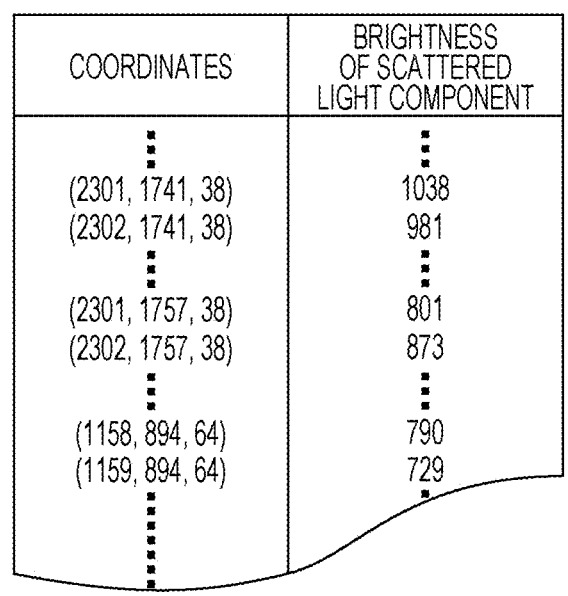
FIG. 21 illustrates an example of the details of the information stored in a storage unit according to the second embodiment.

FIG. 21 illustrates an example of the details of the information stored in the storage unit 320. For each of the plurality of three-dimensional coordinate positions, the storage unit 320 stores the coordinate position in association with the brightness at the coordinate position. 2-3 Image Generation Unit The image generation unit 390 is formed from at least one control circuit, processing circuit, or processor.

Figure 22:
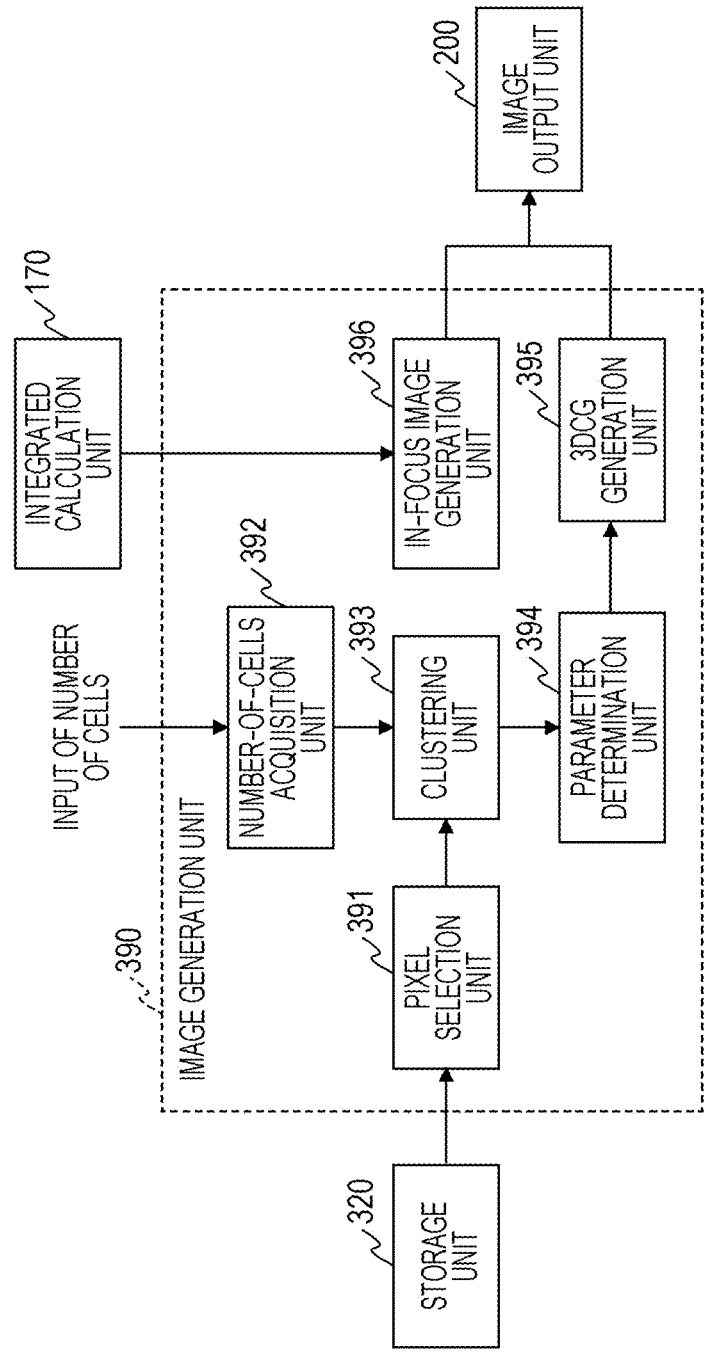
FIG. 22 illustrates an example of the configuration of an image generation unit according to the second embodiment.

FIG. 22 illustrates an example of the configuration of the image generation unit 390. The image generation unit 390 includes a pixel selection unit 391, a number-of-cells acquisition unit 392, a clustering unit 393, a parameter determination unit 394, a 3DCG generation unit 395, and an in-focus image generation unit 396.

The pixel selection unit 391 selects, from among a plurality of pixels stored in the storage unit 320 (that is, the three-dimensional coordinate positions), the ones associated with a brightness value not less than a predetermined value. Although the pixels having a brightness value not less than the predetermined value are selected in this example, pixels having a brightness value not less than a threshold determined on the basis of the overall brightness distribution may be selected. In addition, the range of brightness may be divided into a plurality of groups on the basis of the brightness distribution or predetermined values, and each of the pixels stored in the storage unit 320 may be classified into one of the groups.

The number-of-cells acquisition unit 392 acquires the specified number of cells. For example, the number-of-cells acquisition unit 392 acquires the number of cells input by the user through an input unit (not illustrated). Alternatively, the number-of-cells acquisition unit 392 acquires, from a table describing the relationship between an elapsed time and the number of cells, the number of cells associated with the elapsed time measured by the time measuring unit. The elapsed time is measured from the start of the culture of a tissue, such as a cell or an embryo. The table holds elapsed times from the start of cultivation and information regarding the number of cells at each of the elapsed times. The information is predetermined through experiments.

The clustering unit 393 clusters the pixels selected by the pixel selection unit 391 in the three-dimensional coordinate space into the numbers of cells acquired by the number-of-cells acquisition unit 392. An example of the clustering method is the k-means method.

The parameter determination unit 394 obtains the center and the radius of a sphere of the cell model from the distribution of the pixels in each of the clusters on the basis of the result of clustering performed by the clustering unit 393. That is, the parameter determination unit 394 obtains the center and the radius of a sphere for each of the clusters.

The 3DCG generation unit 395 generates the 3DCG of the sphere having the center and the radius determined by the parameter determination unit 394.

The in-focus image generation unit 396 generates an in-focus image based on the direct light component and an in-focus image based on the light component other than the direct light component by using the brightness of the focal plane based on the direct light component and the brightness of the focal plane based on the light component other than the direct light component generated by the integrated calculation unit 170.

According to the present embodiment, the focal plane determination unit 130 determines the focal plane in accordance with the information received by the focal plane input unit 120. The integrated calculation unit 170 calculates the brightness of each of the pixels on the focal plane, and the in-focus image generation unit 396 generates an in-focus image on the basis of the result of calculation. Alternatively, the in-focus image generation unit 396 may generate the brightness of the coordinate position at which each of the pixels on the focal plane is located by using the brightness at the coordinate position in the three-dimensional space stored in the storage unit 320 and, thus, generate an in-focus image on the focal plane.

The image output unit 200 displays or externally outputs the in-focus image generated by the image generation unit 390 and the 3DCG of the sphere.

2-4 Operation Performed by Image Generation Apparatus

The operation performed by the image generation apparatus 20 having the above-described configuration is described below.

Figure 23:
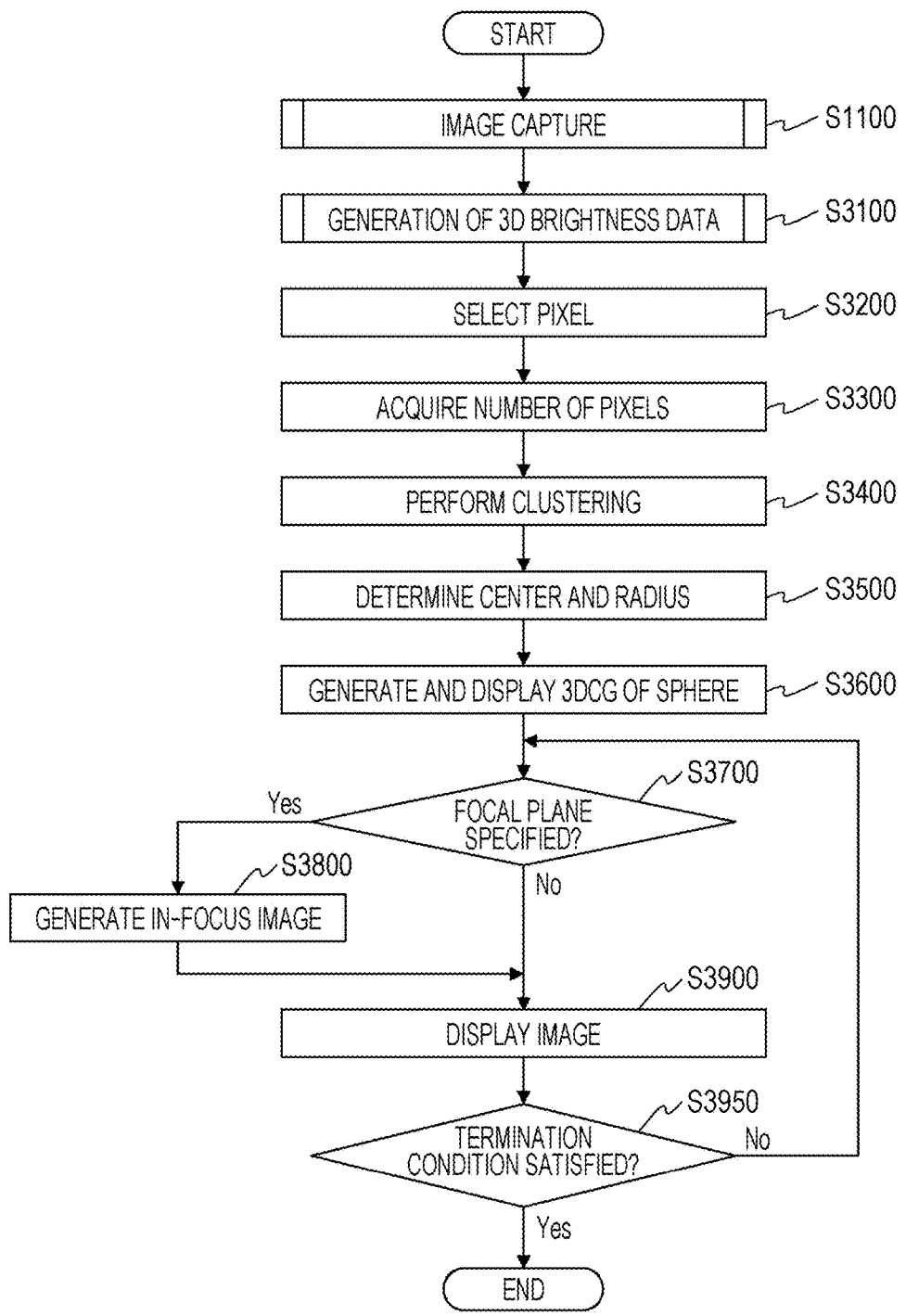
FIG. 23 is a flowchart illustrating an example of the operation performed by the image generation apparatus according to the second embodiment.

FIG. 23 is a flowchart illustrating an example of the operation performed by the image generation apparatus 20 according to the second embodiment.

Step S1100

The image capturing unit 100 sequentially uses each of the plurality of point light sources 141 of the illuminator 140 to illuminate the object with light passing through the mask 142 and captures a plurality of images of the object. Since the image capture in step S1100 is the same as in step S1100 according to the first embodiment, the detailed description of image capture is not repeated.

Step S3100

The integrated calculation unit 170 calculates the brightness of each of the pixels on each of the focal planes in accordance with the information of the plurality of focal planes indicated by the horizontal focal plane list stored in the list holding unit 310 and stores the calculated brightness in the storage unit 320 together with the coordinate value.

The operation performed by the integrated calculation unit 170 is described in detail below.

Step S3200

The pixel selection unit 391 selects, from among the pixels located at the coordinate positions in the three-dimensional coordinate space calculated in step S3100 and stored in the storage unit 320, all of the pixels (that is, points) having brightness values greater than a predetermined value.

Step S3300

The number-of-cells acquisition unit 392 acquires the number of cells input by the user through an input unit (not illustrated).

Step S3400

The clustering unit 393 clusters the plurality of points in the three-dimensional coordinate space selected in step S3200 into clusters of the number of cells acquired in step S3300. For clustering, the k-means method, for example, is used. In this example, clustering is performed by using the k-means method. However, clustering may be performed by using another method, such as the group average method.

Step S3500

For each of the clusters determined in step S3400, the parameter determination unit 394 determines the center (that is, the center coordinate position) and the radius of the sphere corresponding to the cluster on the basis of the distribution of the points in the cluster in the three-dimensional coordinate space. The center of the sphere corresponding to a cluster is the centroid of the points in the cluster. The radius of the sphere corresponding to a cluster is, for example, the radius of a sphere that includes 80% or more of all the points in the cluster and that is the smallest sphere.

Step S3600

The 3DCG generation unit 395 generates, as 3DCG in the three-dimensional coordinate space, spheres each corresponding to one of the clusters equal in number to the number of cells on the basis of the parameters (that is, the center and the radius of the sphere) determined in step S3500. Thereafter, the image output unit 200 displays the spheres formed in 3DCG.

Step S3700

The focal plane input unit 20 determines whether a focal plane has been specified by the user.

If the focal plane is specified by the user (yes in step S3700), the processing proceeds to step S3800. However, if a focal plane is not specified by the user (no in step S3700), the processing proceeds to step S3900.

Figure 24A:
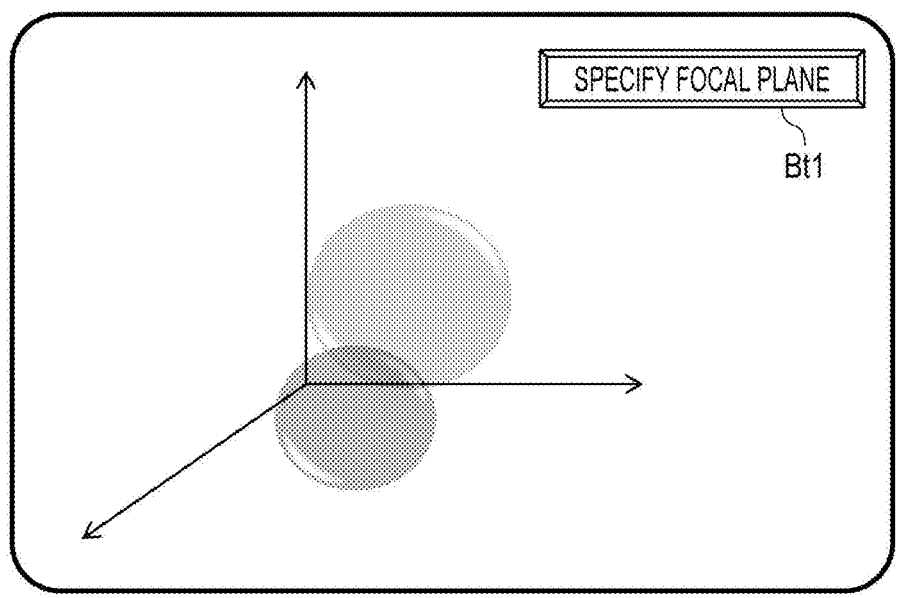
FIG. 24A illustrates an example of display by an image output unit according to the second embodiment.
Figure 24B:
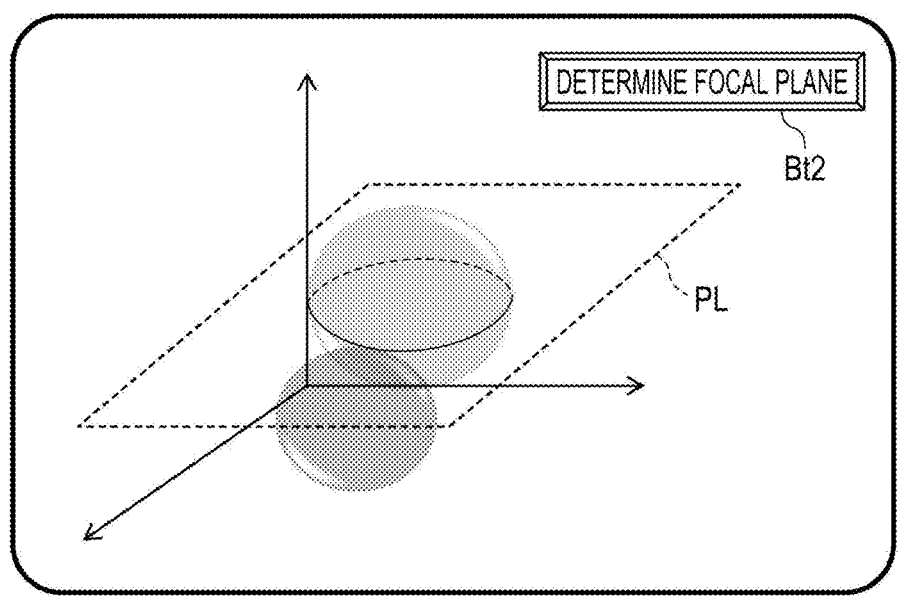
FIG. 24B illustrates an example of display by the image output unit according to the second embodiment.

FIGS. 24A and 24B illustrate examples of images displayed by the image output unit 200. As illustrated in FIG. 24A, the image output unit 200 displays one or more spheres each corresponding to one of the clusters. In addition, the image output unit 200 displays a button Bt1 used to specify a focal plane. The user selects the button Bt1 on the screen having the sphere displayed thereon by clicking the button Bt1. When the button Bt1 is selected, the above-described screen changes to a screen, for example, illustrated in FIG. 24B. The new screen enables the user to specify a focal plane. The screen has a plane PL displayed therein. The plane PL corresponds to a focal plane. The user can move and rotate the displayed plane PL by using a pointing device, such as a mouse. In addition, the screen has a button Bt2 displayed therein. The button Bt2 is used to determine a focal plane. The user moves and rotates the displayed plane PL, places the plane PL at desired position and angle and, thereafter, selects the button Bt2 for determining the focal plane. Thus, the focal plane is specified. Note that according to the present embodiment, the focal plane input unit 120 includes the above-described pointing device and a processing circuit that controls the buttons Bt1 and Bt2 and the plane PL.

Step S3800

The focal plane determination unit 130 acquires the information regarding the position and angle of the focal plane input by the user through the focal plane input unit 120. The integrated calculation unit 170 calculates, for each of the pixels on the focal plane, the brightness based on the direct light component and the brightness based on the light component other than the direct light component in accordance with the information regarding the focal plane acquired by the focal plane determination unit 130. The in-focus image generation unit 396 generates an in-focus image based on the direct light component and an in-focus image based on the light component other than the direct light component by using the brightness of the component of the direct light and the brightness of the light component other than the direct light component at each of the pixels on the focal plane calculated by the integrated calculation unit 170.

Step S3900

The image output unit 200 displays the in-focus image based on the direct light component and the in-focus image based on the light component other than the direct light component, which are generated in step S3800, together with the 3DCG of the spheres generated in step S3600. Note that if the process in step S3900 is performed after step S3700 without performing the process in step S3800, the image output unit 200 displays the 3DCG of the spheres generated in step S3600, as illustrated in FIG. 24A or 24B.

Figure 25A:
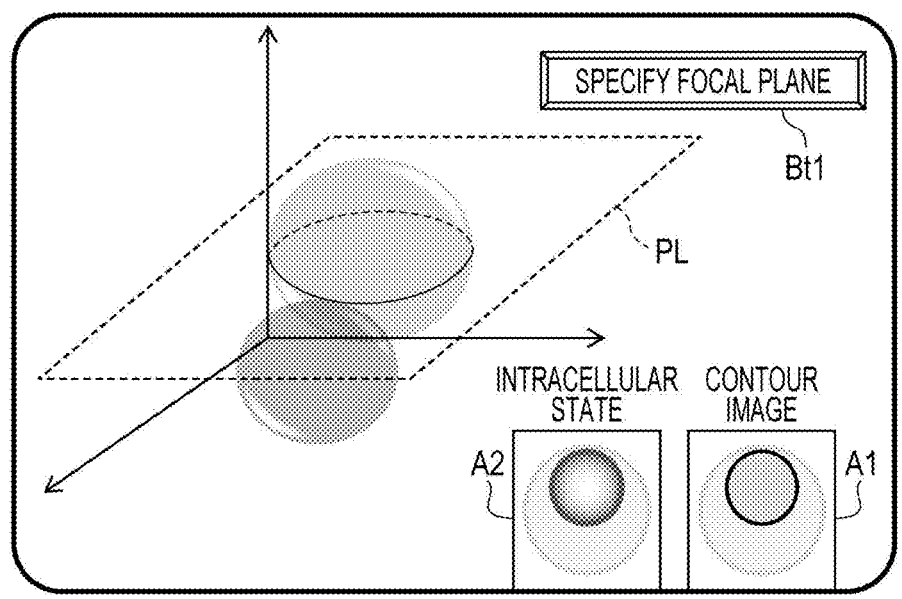
FIG. 25A illustrates another example of display by the image output unit according to the second embodiment.
Figure 25B:
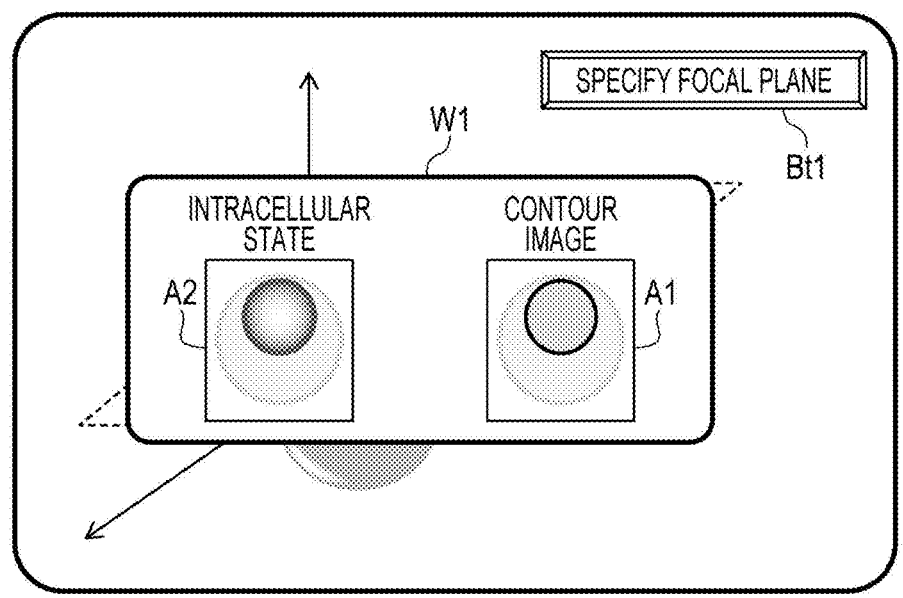
FIG. 25B illustrates another example of display by the image output unit according to the second embodiment.

FIGS. 25A and 25B illustrate another example of images displayed by the image output unit 200. In step S3900, as illustrated in FIG. 25A, the 3DCG of the spheres is displayed. In addition, an in-focus image A1 based on the direct light component generated in step S3800 and an in-focus image A2 based on the light component other than direct light component are displayed. The in-focus image A1 based on the direct light component is displayed as a contour image, and the in-focus image A2 based on the light component other than the direct light component is displayed as an intracellular state. Note that the description of the in-focus images, such as the contour lines and intracellular state, may be made in another form.

In the example illustrated in FIG. 25A, the 3DCG and the in-focus images are displayed side by side in the screen. However, as illustrated in FIG. 25B, the in-focus images may be displayed in a window other than the window for the 3DCG, and the in-focus images may be superimposed over the 3DCG. In addition, when the 3DCG and the in-focus images are displayed side by side, the image generation apparatus 20 may have a function of enlarging or reducing either one of the 3DCG and the in-focus images and displaying the 3DCG and the in-focus images.

Step S3950

After the display operation in step S3900 is performed, the image generation apparatus 20 determines whether the termination condition for generation of the in-focus image and the display operation is satisfied. Examples of the termination condition is that the image generation apparatus 20 has received a termination instruction from the user or that a predetermined time has elapsed since start of the processing in step S3600. If the image generation apparatus 20 determines that the termination condition is not satisfied, the image generation apparatus 20 repeatedly performs the processing that starts from step S3700. By repeating the processing from step S3700 to step S3900, it is possible to display the images formed on a plurality of desired focal planes that the user sequentially inputs, that is, in-focus images and 3DCG indicating the cell arrangement.

However, if the image generation apparatus 20 determines that the termination condition is satisfied, the image generation apparatus 20 ends the process of generating and displaying the in-focus images.

2-5 Operation Performed by Integrated Calculation Unit

The operation performed by the integrated calculation unit 170 in step S3100 is described in detail below.

Figure 26:
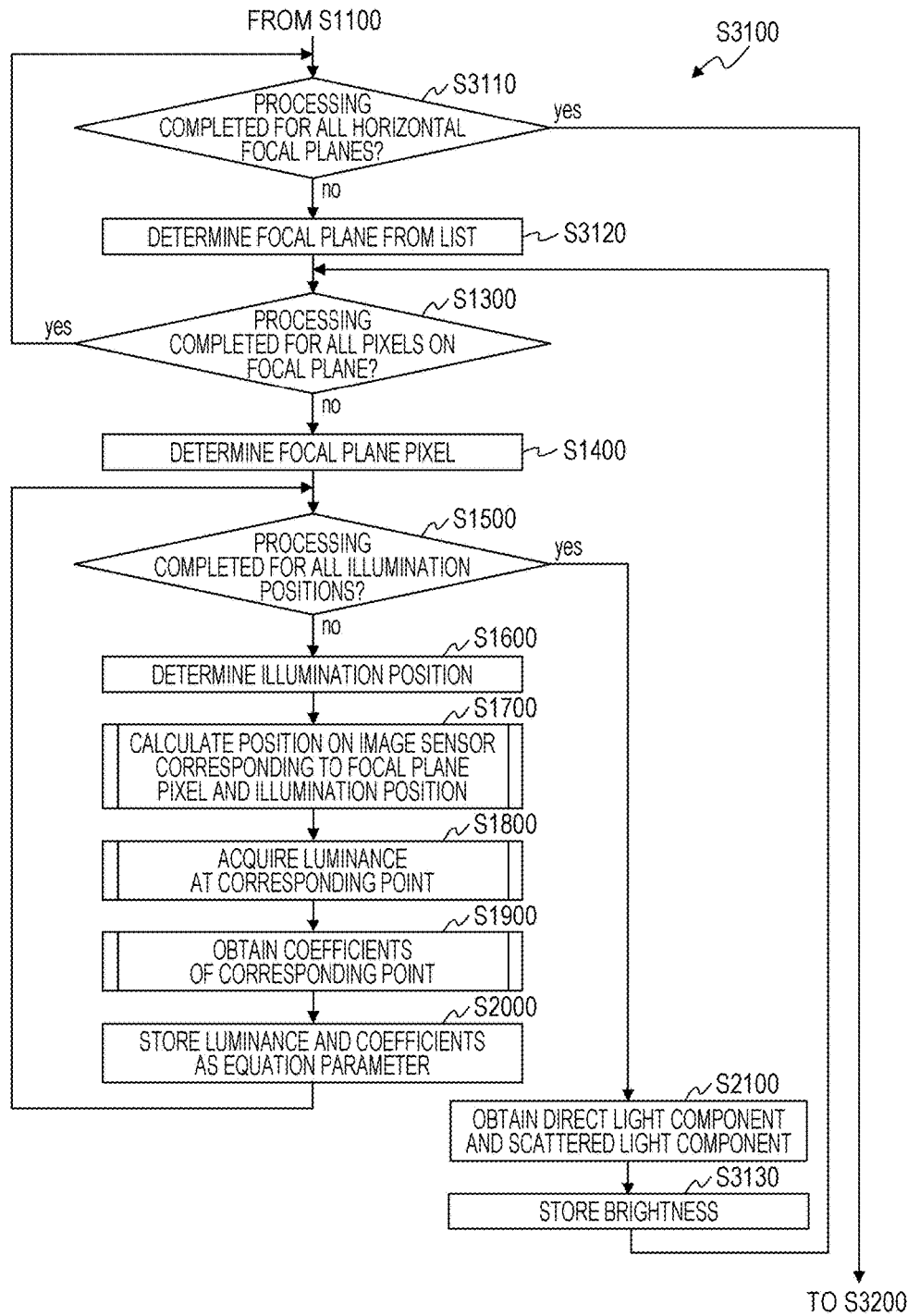
FIG. 26 is a flowchart illustrating the detailed operation performed by an integrated calculation unit according to the second embodiment.

FIG. 26 is a flowchart illustrating the operation performed by the integrated calculation unit 170 in step S3100 in detail. The integrated calculation unit 170 calculates the brightness of the direct light component and the brightness of the light component other than the direct light component on the basis of the processing performed in the following steps S3110 and S3120 by the focal plane determination unit 130.

Step S3110

The focal plane determination unit 130 determines whether the process of calculating the brightness of each of the pixels in all of the horizontal focal planes listed in the horizontal focal plane list in the list holding unit 310 has been completed.

If the calculation of the brightness of all the pixels of all the horizontal focal planes listed in the horizontal focal plane list has been completed (yes in step S3110), the processing proceeds to step S3200. However, if the calculation of the brightness of all the pixels of all the horizontal focal planes listed in the horizontal focal plane list has not been completed (no in step S3110), the processing proceeds to step S3120.

Step S3120

The focal plane determination unit 130 selects, from among all of the horizontal focal planes listed in the horizontal focal plane list, the one that has not been subjected to the brightness calculation process and acquires the information regarding the selected horizontal focal plane. The information regarding the horizontal focal plane is, for example, the coordinate value of the z-axis of the horizontal focal plane.

Step S1300

The corresponding point determination unit 171 refers to the list of the pixels of the predetermined in-focus image on the horizontal focal plane (that is, the generated pixel list) and determines whether determination of the corresponding point is completed for each of all of the pixels listed in the list and located on the horizontal focal plane.

If the determination of corresponding points of all the pixels listed in the generated pixel list has been completed (yes in step S1300), the processing proceeds to step S3110. However, if the determination of the corresponding point of any one of the pixels listed in the generated pixel list has not been completed (no in step S1300), the processing proceeds to step S1400.

Step S1400

The corresponding point determination unit 171 selects, from among the plurality of pixels listed in the generated pixel list, a pixel for which a corresponding point has not yet been determined.

Step S1500

The corresponding point determination unit 171 refers to a predetermined list of illumination positions (that is, the illumination list) and determines whether determination of the corresponding points has been completed for all the illumination positions.

If the determination of corresponding points for all the illumination positions listed in the illumination list has been completed (yes in step S1500), the processing proceeds to step S2100. However, if the determination of the corresponding point of any one of the illumination positions in the illumination list has not been completed (no in step S1500), the processing proceeds to step S1600.

Step S1600

The corresponding point determination unit 171 selects, from among the plurality of illumination positions listed in the illumination list, the one for which the corresponding point has not yet been determined.

Step S1700

The corresponding point determination unit 171 obtains, as the corresponding point, the intersection point of the straight line extending between the illumination position determined in step S1600 and the pixel position on the in-focus image to be generated determined in step S1400 and the surface of the image sensor 150.

Step S1800

The equation generation unit 173 acquires, from the storage unit 110, the captured image corresponding to the illumination position determined in step S1600, that is, the image captured when the point light source 141a at the illumination position is energized. Thereafter, the equation generation unit 173 obtains, from the acquired captured image, the brightness at the position of the corresponding point determined in step S1700.

Step S1900

The equation generation unit 173 refers to the coefficient map and obtains the coefficients corresponding to the illumination position determined in step S1600 and the corresponding point determined in step S1700.

Step S2000

The equation generation unit 173 stores the brightness of the corresponding point acquired in step S1800 and the coefficients acquired in step S1900 as equation parameters. Thereafter, the processing from step S1500 to step S2000 is repeated. In this manner, the equation generation unit 173 collects the parameters necessary for a determinant for solving each of the direct light component Direct and the light component $Global_i$ other than the direct light for the pixel on the focal plane selected in step S1400. As a result, the determinant is generated.

Step S2100

The calculation unit 174 solves the determinant generated by the equation generation unit 173 by using the least squares method. Thus, the calculation unit 174 obtains the brightness of the direct light component and the brightness of the light component other than the direct light component on the pixel of the focal plane selected in step S1400.

Step S3130

The storage unit 320 stores the brightness of the light component other than the direct light component calculated in step S2100 together with the coordinates of the pixel on the focal plane determined in step S1400. After the process in step S3130 is performed, the process in step S1300 is performed again. As a result, the processing from step S1300 to step S3130 is repeated. Consequently, for each of all the pixels on the focal plane, the brightness of the light component other than the direct light component at the position of the pixel is stored in the storage unit 320.

Effect

As described above, according to the image generation apparatus 20 of the second embodiment, light is emitted from the plurality of point light sources 141 located at different positions onto an object and the image sensor 150 through the mask 142 having a pattern in which a light-shielding portion and a light-transmitting portion are repeatedly arranged, such as a slit or checkered pattern. Thereafter, the image generation apparatus 20 captures the image of the object illuminated by the transmitted light passed through the mask 142. In addition, for each of the pixels of the image acquired through the image capture, the image generation apparatus 20 can separate the direct light component from the light component other than the direct light component and perform refocusing calculation at the same time. Furthermore, the image generation apparatus 20 can generate an in-focus image based on the direct light component and an in-focus image based on the light component other than direct light component on a desired focal plane. Still furthermore, by storing the brightness of the light component other than the direct light component on a plurality of focal planes each parallel to the surface of the image sensor 150 together with the three-dimensional coordinate position, a region of the object having a large amount of scattering substance can be identified in the three-dimensional space. More specifically, the position of the cell can be identified in the three-dimensional space. Thus, the image generation apparatus 20 can provide the stereoscopic information regarding the object to the user, and the user can select a focal plane that is more effective for the three-dimensional structure.

According to the second embodiment, the storage unit 320 holds the brightness values of light components other than direct light components, and the information stored in the storage unit 320 is used when the 3DCG of a sphere indicating the cell position is generated. However, the storage unit 320 may store the brightness values of the direct light components calculated by the integrated calculation unit 170 for the pixels on the focal plane, together with the brightness values of the light components other than the direct light components and the coordinate positions of the pixels. In this case, when generating the in-focus image based on the direct light components and the in-focus image based on the light components other than the direct light components in step S3800, the image generation unit 390 may perform interpolation on the coordinate positions of the pixels in the three-dimensional coordinate space stored in the storage unit 320. Thus, the brightness value of the direct light component and the brightness value of the light component other than the direct light component at the coordinate position of the in-focus image are obtained, and two in-focus images are generated.

While the second embodiment has been described with reference to use of the brightness value of the light component other than the direct light component in order to determine the position of the cell, the brightness value of the direct light component may be used. Among the brightness values of the light components other than the direct light components, a relatively high brightness value indicates the position at which a scattering substance of the object is located, whereas the brightness value of the direct light component indicates a boundary surface of the object. More specifically, if the normal to the boundary surface is located on the focal plane, the brightness of the direct light component on the boundary surface decreases. Therefore, among the brightness values of the direct light components, a relatively low brightness value indicates a boundary surface or a contour line.

In addition, according to the second embodiment, among the plurality of points (pixels), the points having brightness values of light components other than direct light components that are greater than or equal to a threshold value are clustered. For each of the clusters, a sphere that includes 80% of all the points belonging to the cluster around the centroid of the cluster is set. However, for example, a boundary surface that includes the largest number of points belonging to the same cluster may be extracted on the basis of the brightness distribution of the direct light components. More specifically, when the object is an early embryo, the cell position inside the embryo is extracted on the basis of the brightness value of the light component other than the direct light component. Thereafter, the embryonic membrane, which is a boundary surface of the embryo, and a cell membrane, which is a boundary surface of the internal cell, are extracted on the basis of the brightness value of the direct light component. In addition, the position of the cell may be restricted by the boundary surface of the embryo, the number of cells may be identified by the boundary surface of the cell, or clustering using the brightness value of the light component other than the direct light component may be restricted by determining the difference between the sizes of cells. In this manner, the 3DCG parameters can be generated more accurately and, thus, the 3DCG with higher accuracy can be generated.

Other Embodiments

While the image generation apparatuses according to one or more aspects have been described above with reference to the embodiments and the modification of the embodiments, the present disclosure is not limited to the embodiments and the modification of the embodiments. A variety of modifications conceivable by those skilled in the art and applied to the above-described embodiments or the modification of the embodiments and an embodiment configured by combining constituent elements of different embodiments without departing from the scope of the present disclosure may be encompassed in the scope of the present disclosure.

For example, while the first and second embodiments have been described above with reference to the generated in-focus image based on the direct light component and in-focus image based on the light component other than the direct light component, at least one of these in-focus images may be generated.

Note that according to the above-described embodiments and the modifications, each of the constituent elements may be implemented by using dedicated hardware or execution of a software program suitable for the constituent element. Each of the constituent elements may be implemented by a program execution unit, such as a central processing unit (CPU) or a processor, reading out and executing a software program recorded on a recording medium, such as a hard disk or a semiconductor memory. The software program used to implement the image generation apparatuses and the like according to the above-described embodiments or modifications is a program that causes a computer to execute the process in each of the steps included in the flowcharts illustrated in FIGS. 13, 15, 16, 18, 23 and 26.

Furthermore, according to the present disclosure, all or some of the units and devices or all or some of the functional blocks in the block diagrams illustrated in FIGS. 1 to 3 and FIGS. 20 and 22 may be implemented by one or more electronic circuits including a semiconductor device, a semiconductor integrated circuit (IC), or large scale integration (LSI). The LSI or IC may be integrated in one chip or may be formed by combining a plurality of chips. For example, the functional blocks other than memory elements may be integrated in one chip. The terms "LSI" and "IC" are used herein, but the terms "system LSI", "very large scale integration (VLSI)" or "ultra large scale integration (ULSI)" may be used as well depending on the level of integration. A field programmable gate array (FPGA), which is programmable after fabrication of the LSI, or a reconfigurable logic device which allows reconfiguration of connections and settings of circuit cells in LSI may be used for the same purpose.

Furthermore, all or some of the functions or the operations of a unit, a device, or part of the device may be performed by software processing. In this case, the software is recorded on one or more non-transitory recording media, such as a ROM, an optical disc, a hard disk drive. When the software is executed by a processing unit (a processor), the software causes the processing unit (the processor) and peripheral devices to perform a specific functions in the software. The system or the device may include one or more non-transitory recording media having the software recorded therein, the processing unit (the processor), and a required hardware device (for example, an interface).

The present disclosure can be widely used in, for example, apparatuses for generating the image of, for example, clumps of cells, or an embryos in culture. The present disclosure is useful to capture the image of an object in an incubator.

What is claimed is:

1. An image generation apparatus comprising:
   a first light source;
   a second light source located a predetermined distance away from the first light source;
   an image sensor on which a translucent substance is disposed;
   a mask located between the image sensor and the first and second light sources, the mask having a light-transmitting portion that transmits light emitted from the first light source and light emitted from the second light source and a light-shielding portion that blocks light emitted from the first light source and light emitted from the second light source; and
   a processing circuit,
   wherein the image sensor acquires a first image of the substance when the first light source is energized and acquires a second image of the substance when the second light source is energized, the first image has a plurality of first pixel regions, and the second image has a plurality of second pixel regions,
   wherein the processing circuit (a) acquires information regarding a focal plane located between the image sensor and the mask and having a plurality of focal points, (b) acquires, for each of the first pixel regions, a ratio of first light including direct light that is emitted from the first light source, travels straight without being refracted and/or scattered, and is incident on the image sensor, and a ratio of second light including light other than the direct light that is emitted from the first light source and is incident on the image sensor, acquires, for each of the second pixel regions, a ratio of third light including direct light that is emitted from the second light source, travels straight without being refracted and/or scattered, and is incident on the image sensor, and a ratio of fourth light including light other than the direct light that is emitted from the second light source and is incident on the image sensor, (c) acquires, by using pixel values of the plurality of the first pixel regions of the first image, pixel values of the plurality of the second pixel regions of the second image, the ratio of the first light, the ratio of the second light, the ratio of the third light, and the ratio of the fourth light, a pixel value based on the first light and the third light for each of the plurality of focal points or a pixel value based on the second light and the fourth light for each of the plurality of focal points, and (d) generates a cross-sectional image of the substance on the focal plane by using the pixel value based on the first light and the third light for each of the plurality of focal points or the pixel value based on the second light and the fourth light for each of the plurality of focal points.

2. The image generation apparatus according to claim 1, wherein in operation (c), letting $\alpha 1$, $\beta 2$, $\alpha 2$, $\beta 2$, L1, and L2 be the ratio of the first light, the ratio of the second light, the ratio of the third light, the ratio of the fourth light, the pixel value of the first pixel region, and the pixel value of the second pixel region corresponding to one of the plurality of focal points, respectively, a pixel value D based on the first light and the third light corresponding to the focal point and a pixel value G based on the second light and the fourth light corresponding to the focal point are obtained by solving the following equation by using a least squares method:

$$\begin{bmatrix} L1 \\ L2 \end{bmatrix} = \begin{bmatrix} \alpha 1 & \beta 1 \\ \alpha 2 & \beta 2 \end{bmatrix} \begin{bmatrix} D \\ G \end{bmatrix}.$$

3. A method for generating an image using a first light source, a second light source located a predetermined distance away from the first light source, an image sensor on which a translucent substance is disposed, and a mask located between the image sensor and the first and second light sources and having a light-transmitting portion that transmits light emitted from the first light source and light emitted from the second light source and a light-shielding portion that blocks light emitted from the first light source and light emitted from the second light source, the method comprising:
   (a) acquiring a first image of the substance by using the image sensor when the first light source is energized, where the first image has a plurality of first pixel regions;
   (b) acquiring a second image of the substance by using the image sensor when the second light source is energized, where the second image has a plurality of second pixel regions;
   (c) acquiring information regarding a focal plane located between the image sensor and the mask and having a plurality of focal points;
   (d) acquiring, for each of the first pixel regions, a ratio of first light including direct light that is emitted from the first light source, travels straight without being refracted and/or scattered, and is incident on the image sensor, and a ratio of second light including light other than the direct light that is emitted from the first light source and is incident on the image sensor;

(e) acquiring, for each of the second pixel regions, a ratio of third light including direct light that is emitted from the second light source, travels straight without being refracted and/or scattered, and is incident on the image sensor, and a ratio of fourth light including light other than the direct light that is emitted from the second light source and is incident on the image sensor;

(f) acquiring, by using the pixel values of the plurality of the first pixel regions of the first image, pixel values of the plurality of the second pixel regions of the second image, the ratio of the first light, the ratio of the second light, the ratio of the third light, and the ratio of the fourth light, a pixel value based on the first light and the third light for each of the plurality of focal points or a pixel value based on the second light and the fourth light for each of the plurality of focal points; and (g) generating a cross-sectional image of the substance on the focal plane by using the pixel values based on the first light and the third light for each of the plurality of focal points or the pixel values based on the second light and the fourth light for each of the plurality of focal points.

4. An image generation apparatus comprising:

light sources including a 1st light source, . . . a jth light source, . . . , and an nth light source, where j and n are natural numbers and $1 < j \leq n$;

an image sensor having a translucent object placed thereon, the image sensor including a 1st pixel, . . . an ith pixel . . . , and an mth pixel, where i and m are natural numbers and $1 < i \leq m$;

a mask having a portion through which light emitted from the light sources transmits and a portion which blocks light emitted from the light sources; and a processing circuit, wherein, during the jth light source emitting light without the light sources except the jth light source emitting light, the processing circuit causes the image sensor to obtain a pixel value L(1j) of the 1st pixel, a pixel value L(ij) of the ith pixel, . . . , and a pixel value L(mj) of the mth pixel by changing j from 1 to n, wherein the processing circuit determines a pixel value $L(i)_{max}$ representing the largest value among the pixel values $L(i1), \ldots L(ij) \ldots, L(in)$, $\alpha_{ij} = L(ij)/L(i)_{max}$, and $\beta_j = 0.5$ by changing j from 1 to n and changing i from 1 to m, and wherein the processing circuit obtains a direct light component $Direct_i$ at a pixel position i in an in-focus image on the focal plane and a light component $Global_i$ other than the direct light component at the pixel position i by solving the following equation by using the least squares method:

$$\begin{bmatrix} L_{i1} \\ L_{i2} \\ \vdots \\ L_{in} \end{bmatrix} = \begin{bmatrix} \alpha_{i1}\beta_1 \\ \alpha_{i2}\beta_2 \\ \vdots \\ \alpha_{in}\beta_n \end{bmatrix} \begin{bmatrix} Direct_i \\ Global_i \end{bmatrix}, \quad (7)$$

wherein the processing circuit generates an image on a basis of $Direct_i$ and $Global_i$.

* * * * *